United States Patent
Falck et al.

(10) Patent No.: US 6,359,158 B1
(45) Date of Patent: Mar. 19, 2002

(54) METHODS AND PRODUCTS RELATED TO 16-HETE ANALOGS

(75) Inventors: John R. Falck, University Park, TX (US); Martin M. Bednar, North Stonington, CT (US); Cordell E. Gross, South Burlington, VT (US); Michael Balazy, Courtlandt Manor, NY (US)

(73) Assignees: University of Vermont and State Agricultural College, Burlington, VT (US); The University of Texas System Board of Regents, Austin, TX (US); New York Medical College, Valhalla, NY (US)

( * ) Notice: Subject to any disclaimer, the term of this patent is extended or adjusted under 35 U.S.C. 154(b) by 0 days.

(21) Appl. No.: 09/312,159

(22) Filed: May 14, 1999

Related U.S. Application Data

(60) Provisional application No. 60/085,602, filed on May 15, 1998.

(51) Int. Cl.$^7$ .............................................. C07C 59/00
(52) U.S. Cl. ........................ 554/219; 554/213; 554/224
(58) Field of Search ................................ 554/213, 224, 554/219

(56) References Cited

U.S. PATENT DOCUMENTS

| | | |
|---|---|---|
| 5,164,381 A | 11/1992 | Wachter et al. |
| 5,256,538 A | 10/1993 | Aiken et al. |
| 5,334,736 A | 8/1994 | Sun et al. |
| 5,434,186 A | 7/1995 | Cohen et al. |
| 5,466,669 A | 11/1995 | Konig et al. |
| 5,527,890 A | 6/1996 | Rao et al. |
| 5,552,441 A | 9/1996 | Dillard et al. |
| 5,612,377 A | 3/1997 | Crooks et al. |
| 5,753,702 A | 5/1998 | Bednar et al. |

FOREIGN PATENT DOCUMENTS

WO    WO97/44024    11/1997

OTHER PUBLICATIONS

Chem. Abstr., 116:214224, 1992.*
Chem. Abstr., 123:29628, 1995.*
Knickle, L., et al., Mol Pharmacol, 45:6:1273–80, Abstract.
Falck, J.R. et al., The Journal of Biological Chemistry, vol. 265 (18):10244–10249 (1990).
Heckmann, B. et al., Tetrahadron Letters, vol. 37(9):1425–1428 (1996).
Bednar, M.M et al., Abstract from meeting held in Florence, Italy (Jun. 1994).
Ying Zhu et al., Hypertension, vol. 25(4),Part 2:854–859 (Apr. 1995).
Gross, C.E. et al., Neurological Res., vol. 16:465–470 (Dec. 1994).
Lesch, M.E. et al., Agents and Actions, vol. 34:25–27 (1991).
Lee, T.H. et al., The New England Journal of Medicine, vol. 312(19):1217–1224 (May 9, 1985).
Hill, E. et al., Biological Mass Spectrometry, vol. 21:249–253 (1992).

(List continued on next page.)

*Primary Examiner*—Deborah D. Carr
(74) *Attorney, Agent, or Firm*—Wolf, Greenfield & Sacks, P.C.

(57) ABSTRACT

The present invention includes 16-HETE analogs which are agonists and antagonists of 16-HETE. The compositions may be formulated in pharmaceutically acceptable formulations. The invention also includes methods and products for inhibiting neutrophil adhesion and neutrophil aggregation using the 16-HETE agonists. One method of the invention involves the administration of a 16-HETE agonist in combination with a thrombolytic agent to a patient suffering from thromboembolic stroke.

3 Claims, 4 Drawing Sheets

OTHER PUBLICATIONS

Watanabe, Masako et al., Br. J. Pharmacol. 102:239–245 (1991).

Laethem, R.M. et al., The Journal of Biological Chemistry, vol. 268(17):12912–12918 (1993).

Balazy, M., The Journal of Biological Chemistry, vol. 266(35):23561–23567 (1991).

Bednar, M.M. et al., Journal of Thrombosis and Thrombolysis:1:179–185 (1995).

Springer, T.A., Annu. Rev. Cell Biol., 6:359–402 (1990).

Kraemer, R. et al., American Journal of Pathology, vol. 128(3):446–454 (1987).

Hatzelmann A. et al., Euro. J. Biochem. 173:445–452 (1988).

Setty BN, Werner MH, Hannun YA, Stuart MJ; "15-Hydroxyeicosatetraenoic acid-mediated potentiation of thrombin-induced platelet functions occurs via enhanced production of phosphoinositide-derived second messengers—sn–1,2–diacylglycerol and inositol–1,4,5–trisphosphate."; *Blood;* 80(11):2765–73, Dec. 1, 1992.

Luo G, Zeldin DC, Blaisdell JA, Hodgson E, Goldstein JA; "Cloning and expression of murine CYP2Cs and their ability to metablolize arachidonic acid," *Archives of Biochemistry and Biophysics:* 357(1):45–57, Sep. 1, 1998.

Chemical Abstracts AN 1995:138771, Takada et al., Jan. 1994.

Chemical Abstracts AN 1990:493392, Falck et al., Jan. 1990.

Chemical Abstracts AN 1994:474474, Knickle et al., Jan. 1994.

* cited by examiner

LTB₄ SYNTHESIS

16(R)-HETE ANALOGS
EFFECT ON NEUTROPHIL AGGREGATION

METHODS AND PRODUCTS RELATED TO 16-HETE ANALOGS

This applications claims benefit of Prov. No. 60/085,602 filed May 15, 1998.

FIELD OF THE INVENTION

The present invention relates to 16-HETE analogs which are agonists and antagonists of 16-HETE. The invention also relates to methods and products for inhibiting neutrophil adhesion and neutrophil aggregation using the 16-HETE agonists.

BACKGROUND OF THE INVENTION

The inflammatory response is an important element of a host's natural defense mechanism against pathogens. It also is involved in wound healing. Despite the beneficial role that the inflammatory response plays in host survival, excessive inflammation may have clinically adverse results in some medical conditions.

Leukocytes are a major cellular component of inflammatory and immune responses. This class of cells includes neutrophils, lymphocytes, monocytes, eosinophils, and basophils. Neutrophils, which play a key role in the inflammatory response, are generally present within the body in a resting unstimulated state. Once stimulated, the neutrophils migrate to the site of injury and release toxic factors.

The migratory capability of a neutrophil is dependent on the ability of the neutrophil to alter its adhesive properties. In a resting unstimulated state a neutrophil is not adhesive and cannot migrate. Once the neutrophil has been stimulated, however, it becomes more adhesive and is capable of migrating. The increase in neutrophil adhesiveness causes the stimulated neutrophil to aggregate and to adhere to endothelium. Stimulation of the neutrophil also causes the neutrophil to undergo diapedesis, which involves the migration of the neutrophil between post-capillary endothelial cells into the tissues.

In the tissues, an activated neutrophil releases enzymes such as collagenase and elastase, among others. Neutrophil stimulation may also initiate a burst of oxygen consumption, with concomminant activation of the hexose-monophosphate shunt and activation of nicotinamide-adenine dinucleotide phosphate (NADPH) oxidase. Activation of these systems results in the formation and release of factors such as hydrogen peroxide and hydroxyl radicals, which are toxic to microorganisms and tumor cells, and thereby facilitating the destruction of the injury causing agent.

Several studies have focused on analyzing the control and regulation of the adhesive properties of neutrophils. Much of this research has centered on adhesion receptors and also on metabolites of arachidonic acid such as C20 carbon fatty acid found in every cell membrane. Arachidonic acid metabolism occurs by different mechanisms in stimulated versus unstimulated neutrophils and results in the production of a different spectrum of metabolites in stimulated versus unstimulated neutrophils.

In stimulated neutrophils, the cytochrome P450 mixed function oxidase system appears to be more active. Moreover, during neutrophil stimulation, 5-lipoxygenase is translocated to the membrane compartment fraction, where it produces 5-hydroperoxyeicosatetraenoic acid (5-HPETE). 5-HPETE is then either metabolized to 5-hydroxyeicosatetraenoic acid (5-HETE) by peroxidase or dehydrated to form leukotriene $A_4$. Leukotriene $A_4$ is converted into leukotriene $B_4$ which is a potent chemotactic agent and promoter of neutrophil adhesion.

In unstimulated neutrophils, the metabolism of arachidonic acid is markedly different than that in stimulated neutrophils. The metabolism of arachidonic acid in unstimulated neutrophils is sensitive to cytochrome P450 inhibitors but not to cyclooxygenase or lipoxygenase inhibitors. Hatzelmann and Ullrich characterized the metabolites produced in unstimulated neutrophils, reporting the finding that arachidonic acid is metabolized to 20-HETE and 15-HETE. *Hatzelmann, Eur. J. Biochem.* 173, 445–452 (1988). Another study, Kraemer et al., found that the arachidonic acid metabolic products formed in unstimulated neutrophils exhibited a potent anti-aggregatory activity toward human neutrophils, suggesting that the identified arachidonic acid metabolites may play some role in the regulation of neutrophil adhesion and aggregation properties. *Kraemer et al., Am. J. Pathol.* 128, 446–454 (1987).

SUMMARY OF THE INVENTION

It was recently discovered in co-pending U.S. patent application Ser. No. 08/652,327, filed May 22, 1996 and issued as U.S. Pat. No. 5,753,702 on May 19, 1998 and PCT Patent Application No. PCT/US97/08865, and its related national Stage U.S. patent application Ser. No. 09/194,166, the entire contents of which are hereby incorporated by reference, that 16-HETE (16-hydroxyeicosatetraenoic acid) is a component of arachidonic acid metabolism in neutrophils and that 16-HETE is a potent inhibitor of neutrophil adhesion and neutrophil aggregation. It was also disclosed in these applications that 16-HETE when administered alone actually reduces the size of brain infarcts resulting from acute stroke relative to the size of brain infarcts which occur in the absence of a therapeutic. When 16-HETE is administered in combination with clot lysing thrombolytic agents such as tPA, the therapeutic combination actually reduces the size of brain infarcts resulting from acute stroke relative to the size of brain infarcts which occur in a subject suffering from an acute stroke who has been treated only with a thrombolytic agent such as tPA.

The present invention relates to novel analogs of 16-HETE. Some of the analogs of 16-HETE are agonists which maintain the biological activity of 16-HETE but which are more stable and have longer half-lives. The 16-HETE analogs also include 16-HETE antagonists which inhibit the activity of 16-HETE. These antagonists are useful when it is desirable to prevent inhibition of neutrophil activity.

According to one aspect of the invention, compositions are provided. These compositions include the following 16-HETE analog:

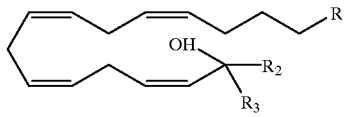

wherein R is selected from the group consisting of —C(O)—X—$SO_2$—$R_1$, —C(O)—X—CO—$R_1$, —C(O)—X—C(OH)$_2$—$R_1$, —C(O)—X—C(NH)$_2$—$R_1$, —C(O)—X—C(NH$_2$)$_2$—$R_1$, piperonyl, —CN, —OR', —SR', —NO$_2$, —NR'R', amino acid, —C(O)R', —C(S)R', —C(O)OR', —C(S)OR', —C(O)SR, —C(S)SR', —C(O)N(R')$_2$, —C(O)C(O)R', —C(S)C(O)R', —C(O)C(S)R', —C(S)C(S)R', —C(O)C(O)OR', —C(S)C(O)OR', —C(O)C(S)OR', —C(O)C(O)SR', —C(S)C(S)OR', —C(S)C(O)SR', —C(O)C(S)SR', —C(S)C(S)SR', —C(O)C(O)N(R')$_2$, —C(S)C(O)N(R')$_2$, —C(O)C(S)N(R')$_2$, or —C(S)C(S)N(R')$_2$; wherein X is selected from the group consisting of O, N, and a bond; wherein R$_1$, R$_2$, and R$_3$ each independently is selected from the group consisting of hydrogen, alkyl, alkenyl, alkynyl, alkoxy, aryl, and heteroaryl; wherein each R' is (CH$_2$)$_z$—NR"R" and wherein R" is independently selected from the group consisting of (C$_1$–C$_6$) alkyl, (C$_1$–C$_6$) alkenyl, (C$_1$–C$_6$) alkoxy, (C$_1$–C$_6$) alkynyl, (C$_6$–C$_{20}$) aryl, (C$_6$–C$_{20}$) substituted aryl, (C$_6$–C$_{26}$) alkaryl, substituted (C$_6$–C$_{26}$) alkaryl, and (C$_5$–C$_7$) heteroaryl.

16-HETE analogs include both agonists and antagonists. In some embodiments the 16-HETE agonists have the following general structure:

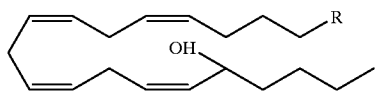

wherein either R$_1$ or R$_2$ is a C$_3$ alkyl and the other is a hydrogen.

In one embodiment R$_1$, R$_2$, and R$_3$ each independently is selected from the group consisting of hydrogen, (C$_1$–C$_6$) alkyl, (C$_1$–C$_6$) alkenyl, (C$_1$–C$_6$) alkynyl, and (C$_1$–C$_6$) alkoxy.

In another embodiment the 16-HETE analog has the following structure:

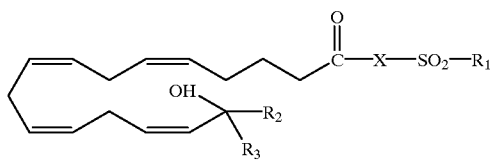

In a preferred embodiment X is NH and R$_2$ and/or R$_3$ is hydrogen. In another preferred embodiment R$_3$ is a C$_3$ alkyl. Preferably, the 16-HETE analog has the following structure:

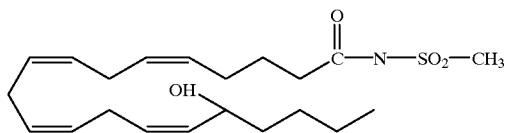

In a preferred embodiment X is O and R$_2$ and/or R$_3$ is hydrogen. In another preferred embodiment R$_3$ is a C$_3$ alkyl.

In other preferred embodiments the 16-HETE analog is one of the following structures:

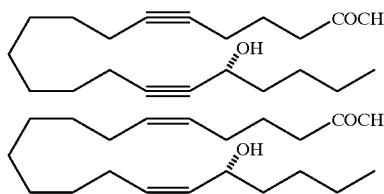

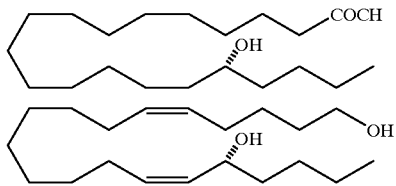

In another embodiment the 16-HETE analog is a 16-HETE antagonist having the following general structure:

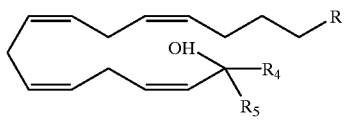

wherein R$_4$ and R$_5$ each independently is selected from the group consisting of hydrogen, C$_{1-2}$ alkyl, C$_{4-6}$ alkyl, alkenyl, alkynyl, alkoxy, aryl, and heteroaryl and wherein when either R$_1$ or R$_2$ is a C$_3$ alkyl the other is not a hydrogen.

According to another aspect of the invention the 16-HETE analog has the following structure:

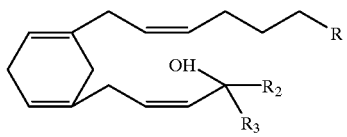

wherein R is selected from the group consisting of —C(O)—X—SO$_2$—R$_1$, —C(O)—X—CO—R$_1$, —C(O)—X—C(OH)$_2$—R$_1$, —C(O)—X—C(NH)$_2$—R$_1$, —C(O)—X—C(NH$_2$)$_2$—R$_1$, piperonyl, —CN, —OR', —SR', —NO$_2$, —NR'R', amino acid, —C(O)R', —C(S)R', —C(O)OR', —C(S)OR', —C(O)SR, —C(S)SR', —C(O)N(R')$_2$, —C(O)C(O)R', —C(S)C(O)R', —C(O)C(S)R', —C(S)C(S)R', —C(O)C(O)OR', —C(S)C(O)OR', —C(O)C(S)OR', —C(O)C(O)SR', —C(S)C(S)OR', —C(S)C(O)SR', —C(O)C(S)SR', —C(S)C(S)SR', —C(O)C(O)N(R')$_2$, —C(S)C(O)N(R')$_2$, —C(O)C(S)N(R')$_2$, or —C(S)C(S)N(R')$_2$; wherein X is selected from the group consisting of O, NH, and a bond; wherein R$_1$, R$_2$, and R$_3$ each independently is selected from the group consisting ol hydrogen, alkyl, alkenyl, alkynyl, alkoxy, aryl, and heteroaryl; wherein each R' is (CH$_2$)$_z$—NR"R" and wherein R" is independently selected from the group consisting of (C$_1$–C$_6$) alkyl, (C$_1$–C$_6$) alkenyl, (C$_1$–C$_6$) alkoxy, (C$_1$–C$_6$) alkynyl, (C$_6$–C$_{20}$) aryl, (C$_6$–C$_{20}$) substituted aryl, (C$_6$–C$_{26}$) alkaryl, substituted (C$_6$–C$_{26}$) alkaryl, and (C$_5$–C$_7$) heteroaryl.

In one embodiment R$_1$, R$_2$, and R$_3$ each independently is selected from the group consisting of hydrogen, (C$_1$–C$_6$) alkyl, (C$_1$–C$_6$) alkenyl, (C$_1$–C$_6$) alkynyl, and (C$_1$–C$_6$) alkoxy.

In another embodiment the 16-HETE analog has the following structure:

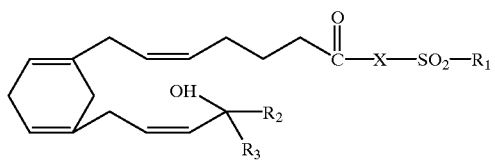

In a preferred embodiment X is NH and $R_2$ and/or $R_3$ is hydrogen. In another preferred embodiment $R_3$ is a $C_3$ alkyl. Preferably, the 16-HETE analog has the following structure:

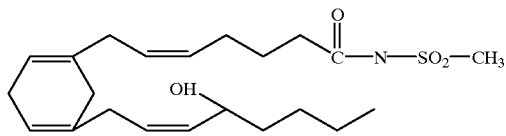

In a preferred embodiment X is O and $R_2$ and/or $R_3$ is hydrogen. In another preferred embodiment $R_3$ is a $C_3$ alkyl. In another preferred embodiment the 16-HETE analog has the following structure:

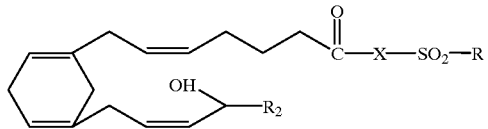

Several diseases or conditions are characterized by excessive inflammation associated with neutrophil adhesion and neutrophil aggregation. The present invention provides compositions for inhibiting neutrophil adhesion and neutrophil aggregation as well as for treating subjects having diseases or conditions characterized by excessive inflammation associated with neutrophil adhesion and neutrophil aggregation. In some embodiments the composition is a pharmaceutical composition of a 16-HETE agonist. In these embodiments the 16-HETE agonist is present in a therapeutically effective amount for treating an adverse medical condition mediated by neutrophil adhesion and/or neutrophil aggregation. In an embodiment, the pharmaceutical preparation of the invention includes other therapeutic agents for treating the adverse medical condition mediated by neutrophil adhesion and/or neutrophil aggregation. For instance when the medical condition is an inflammatory disease the other therapeutic agents are agents for treating an inflammatory disease or condition. According to particular embodiments of the invention the therapeutic agent for treating the inflammatory disease or condition is selected from the group consisting of antibiotics, such as tetracycline antibiotics, aminoglycosides, macrolides, lincomycins, penicillanic acid (6-APA)- derivatives having 6β-acylamino groups, cephalosporanic acid (7-ACA)-derivatives having 7β-acylamino groups, penicillanic acid, β-lactam antibiotics of the clavam, penem and carbapenen type, and antibiotics of the bicozamycin, novobiocin, chloramphenicol or thiamphenicol, rifampicin, fosfomycin, colistin and vancomycin and antiphlogistics, such as glucocorticoids, immunosuppressive agents, penicillamine, hydroxychloroquine, and nonsteroidal inflammation-inhibitors.

According to another embodiment, the pharmaceutical preparation includes therapeutic agents for treating an ischemic disease or condition. Preferably the therapeutic agent is selected from the group consisting of: anticoagulation agents, such as heparin, warfarin, coumadin, dicumarol, phenprocoumon, acenocoumarol, ethyl biscoumacetate, and indandione derivatives; antiplatelet agents, such as aspirin, thienopyridine, dipyridamole and sulfinpyrazone; and thrombolytic agents, such as plasminogen, $a_2$-antiplasmin, streptokinase, antistreplase, tissue plasminogen activator, and urokinase.

According to one preferred embodiment of the invention, the pharmaceutical preparation includes the 16-HETE agonist of the invention together with a thrombolytic agent. The pharmaceutical preparation is formulated for intravenous administration in one embodiment. In another embodiment the thrombolytic agent is recombinant tPA. In another embodiment the thrombolytic agent is a modified tPA. In one embodiment the modified tPA is T103N, N117Q, KHRR (296–299) AAAA tPA. In another embodiment the modified tPA is a vampire bat tPA selected from the group consisting of Bat-Pa(H), Bat-Pa(I), and Bat-PA(L).

The invention also provides a composition of 16-HETE analog for use as a medicament.

The invention also provides a composition of 16-HETE agonist for use in the manufacture of a medicament for the treatment of adverse medical conditions mediated by neutrophil adhesion and/or neutrophil aggregation. In another embodiment the invention provides a composition of 16-HETE agonist for use in the manufacture of a medicament for the treatment of an inflammatory disease or condition. In another embodiment the invention provides a composition of 16-HETE agonist for use in the manufacture of a medicament for the treatment of an ischemic disease or condition, including but not limited to, acute stroke.

The invention also encompasses methods of treatment. According to another aspect of the invention the 16-HETE agonist may be administered to a subject in conjunction with other drugs for treating an adverse medical condition mediated by neutrophil adhesion and/or neutrophil aggregation. In one embodiment the condition mediated by neutrophil adhesion and/or neutrophil aggregation is an inflammatory disease or condition. According to particular embodiments, the inflammation is characteristic of or results from meningitis, cerebral edema, arthritis, nephritis, adult respiratory distress syndrome, pancreatitis, myositis, neuritis, connective tissue disease, phlebitis, arteritis, vasculitis, allergy, anaphylaxis, gout, ulcerative colitis, and/or ehrlichiosis. In one embodiment the method also includes the step of administering to the subject a therapeutic agent other than and in addition to 16-HETE agonist for treating the inflammatory condition. According to another embodiment, the condition mediated by neutrophil adhesion and/or neutrophil aggregation is an ischemic disease or condition. Preferably the ischemic condition is selected from the group consisting of a stroke and a myocardial infarction. In one embodiment the 16-HETE agonist is administered to a subject having an ischemic disease or condition, in conjunction with a thrombolytic agent.

The 16-HETE agonist may be administered by any known method of drug delivery. Preferably the 16-HETE agonist is administered orally or intravenously.

One aspect of the invention is directed to a method for inhibiting neutrophil adhesion and neutrophil aggregation. The method involves contacting neutrophils with a 16-HETE agonist in situ in an amount effective to inhibit neutrophil adhesion and neutrophil aggregation. This aspect of the invention may be applied in vitro or in vivo to inhibit neutrophil adhesion and neutrophil aggregation at a desired time.

In one aspect, the invention is a method for treating thromboembolic stroke. The method involves administering to a subject experiencing an acute thromboembolic stroke 16-HETE agonist in combination with a thrombolytic agent in an amount effective to reduce brain injury which would otherwise occur as a result of the stroke. In one embodiment, the 16-HETE agonist is 16(R)-HETE agonist and the thrombolytic agent is tPA. In another embodiment the 16-HETE agonist and thrombolytic agent are administered to the subject within a first 2–6 hours after the subject experienced the thromboembolic stroke. In one embodiment the 16-HETE agonist is administered in an amount between 0.5 and 20 mg/kg per minute. In a preferred embodiment the 16-HETE agonist is 16(R)-HETE agonist and is administered in an amount of 1.0 mg/kg per minute. In one embodiment the thrombolytic agent is administered in an amount between 0.05 mg/kg and 1.5 mg/kg. In a preferred embodiment the thrombolytic agent is tPA and is administered in an amount of 0.9 mg/kg. In one embodiment the thrombolytic agent is recombinant tPA. In another embodiment the thrombolytic agent is a modified tPA. In one embodiment the modified tPA is T103N, N117Q, KHRR (296–299) AAAA tPA. In another embodiment the modified tPA. is a vampire bat tPA selected from the group consisting of Bat-PA(H), Bat-Pa(I), and Bat-PA(L). In yet another embodiment the modified tPA is C84S tPA.

According to another aspect of the invention a method of inhibiting leukotriene production in a neutrophil is provided. Leukotriene is an arachidonic acid metabolite that is a potent neutrophil chemoattractant and pro-aggregant. It was discovered according to the invention that 16-HETE and agonists thereof inhibit leukotriene production in neutrophils. The method includes the step of administering to a neutrophil, 16-HETE or an agonist thereof in an amount effective to inhibit leukotriene production.

The invention in another aspect is a method of inhibiting leukotriene production in a subject having a condition mediated by leukotriene activity. The method involves the step of administering to said subject having a condition mediated by leukotriene activity a 16-HETE or an agonist thereof in an amount effective to inhibit leukotriene production. In a preferred embodiment the leukotriene is leukotriene $B_4$. In another embodiment the leukotriene production is inhibited in neutrophils.

In one embodiment the condition mediated by leukotriene activity is selected from the group consisting of arthritis, rheumatoid arthritis, osteoarthritis, allergic rhinitis, psoriasis, dermatitis, ischemic induced myocardial injury, reperfusion injury, gout, asthma, adult respiratory distress syndrome, atherosclerosis, inflammatory disease, stroke, spinal cord injury, and traumatic brain injury. Preferably the condition mediated by leukotriene activity is an inflammatory disease.

Each of the limitations of the invention can encompass various embodiments of the invention. It is, therefore, anticipated that each of the limitations of the invention involving any one element or combinations of elements can be included in each method and product.

These and other aspects of the invention, as well as various advantages and utilities, will be more apparent with reference to the detailed description of the preferred embodiments.

BRIEF DESCRIPTION OF THE DRAWINGS

The present invention may be more easily and completely understood when taken in conjunction with the accompanying drawings, in which.

DETAILED DESCRIPTION OF THE INVENTION

Figure 1:
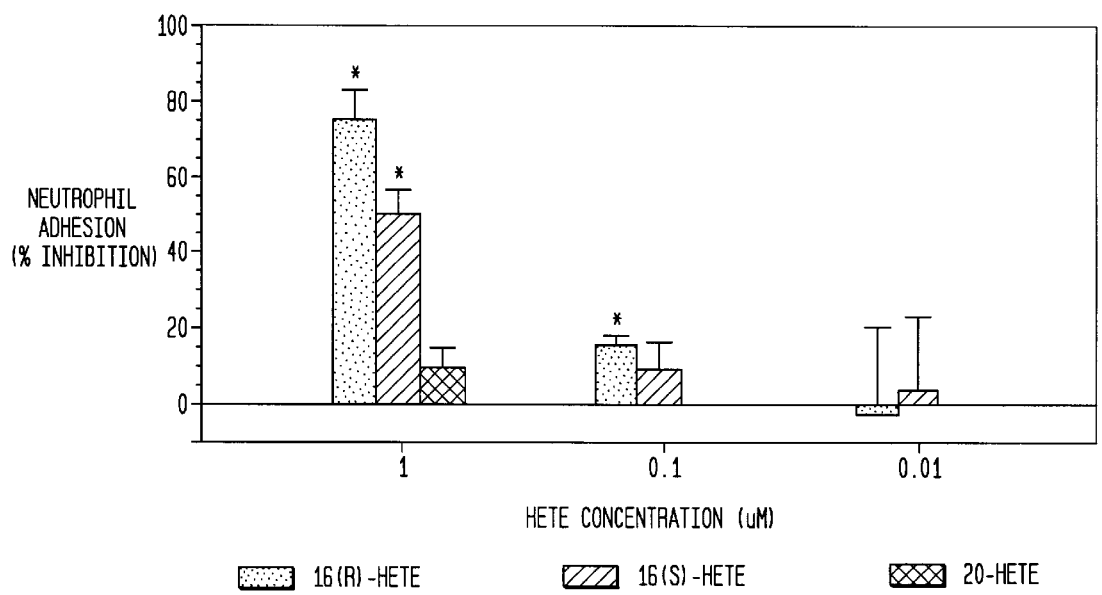
FIG. 1 is a bar graph depicting the percent inhibition of neutrophil adhesion to a gelatin matrix resulting from a 10 minute pre-incubation with 16(R)-HETE, 16(S)-HETE, and 20-HETE on basal human neutrophils.

The invention involves the finding that certain 16-HETE analogs function as agonists and others function as antagonists. Applicants initial discovery that an arachidonic acid metabolic product is effective in inhibiting neutrophil adhesion and neutrophil aggregation is described in co-pending U.S. patent application Ser. No. 08/652,327, filed May 22, 1996 and issued as U.S. Pat. No. 5,753,702 on May 19, 1998 and PCT Patent Application No. PCT/US97/08865, and its related national Stage U.S. patent application Ser. No. 09/194,166. Applicants also discovered that the compound 16-HETE, can be used effectively to inhibit neutrophil adhesion and neutrophil aggregation in both stimulated and unstimulated neutrophils and that 16-HETE is useful as an in vivo therapeutic for reducing the extent of brain infarct damage that occurs during an acute stroke. The 16-HETE agonists described herein have the same biological activity and function as 16-HETE.

The discoveries of the invention have revealed several novel properties of 16-HETE and analogs thereof which indicate that these molecules are particularly advantageous as therapeutics. For instance, 16-HETE and agonists thereof are capable of inhibiting basal and thrombin-stimulated neutrophil adhesion, and fMLP-included neutrophil aggregation. 16-HETE and agonists thereof also decrease the density of a neutrophil cell surface receptor (CD18) involved in neutrophil adhesion. Even though 16-HETE and agonists thereof have this dramatic effect on neutrophils these molecules do not affect platelet activity or function. Additionally, the agonists of 16-HETE have modifications which increase the half-life of these molecules and therefore have sustained therapeutic value.

As demonstrated in the Examples below, 16-HETE also is capable of inhibiting leukotriene production. When 16-HETE is administered to neutrophils, it causes a dramatic inhibition in the production of leukotriene $B_4$, and therefore is useful for preventing neutrophil chemoattraction.

The compounds of the invention are 16-HETE analogs. 16-HETE has the following structural formula:

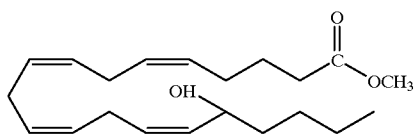

The 16-HETE analogs of the invention have the following structural formulas:

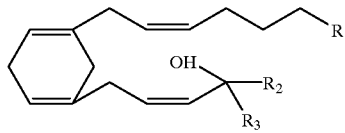

or

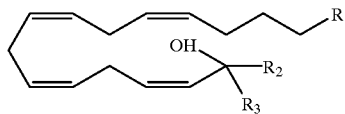

wherein R is selected from the group consisting of —C(O)—X—SO$_2$—R$_1$, —C(O)—X—CO—R$_1$, —C(O)—X—C(OH)$_2$—R$_1$, —C(O)—X—C(NH)$_2$—R$_1$, —C(O)—X—C(NH$_2$)$_2$—R$_1$, piperonyl, —CN, —OR', —SR', —NO$_2$, —NR'R', amino acid, —C(O)R', —C(S)R', —C(O)OR', —C(S)OR', —C(O)SR, —C(S)SR', —C(O)N(R')$_2$, —C(O)C(O)R', —C(S)C(O)R', —C(O)C(S)R', —C(S)C(S)R', —C(O)C(O)OR', —C(S)C(O)OR', —C(O)C(S)OR', —C(O)C(O)SR', —C(S)C(S)OR', —C(S)C(O)SR', —C(O)C(S)SR', —C(S)C(S)SR', —C(O)C(O)N(R')$_2$, —C(S)C(O)N(R')$_2$, —C(O)C(S)N(R')$_2$, or —C(S)C(S)N(R')$_2$; wherein X is selected from the group consisting of O, N, and a bond; wherein R$_1$, R$_2$, and R$_3$ each independently is selected from the group consisting of hydrogen, alkyl, alkenyl, alkynyl, alkoxy, aryl, and heteroaryl; wherein each R' is (CH$_2$)$_z$—NR"R" and wherein R" is independently selected from the group consisting of (C$_1$–C$_6$) alkyl, (C$_1$–C$_6$) alkenyl, (C$_1$–C$_6$) alkoxy, (C$_1$–C$_6$) alkynyl, (C$_6$–C$_{20}$) aryl, (C$_6$–C$_{20}$) substituted aryl, (C$_6$–C$_{26}$) alkaryl, substituted (C$_6$–C$_{26}$) alkaryl, and (C$_5$–C$_7$) heteroaryl.

16-HETE analogs include both agonists and antagonists. As used herein a "16-HETE agonist" is a molecule encompassed by the above formulas wherein either R$_1$ or R$_2$ is a C$_3$ alkyl and the other is a hydrogen and which maintains the biological activity of 16-HETE. The modifications made to the terminal carboxyl group of 16-HETE result in a molecule having an equivalent or better stability than 16-HETE.

In general the 16-HETE agonists are more stable and have a longer half life than native 16-HETE. An effective amount of a 16-HETE agonist for inhibiting neutrophil adhesion/aggregation can easily be assessed by any method known in the art. For example, any of the assays described in the Examples section below which examine the adhesive/aggregatory properties of 16-HETE on neutrophils may be utilized to assess biological activity and effective amounts. These assays include but are not limited to neutrophil adhesion, neutrophil aggregation, CD-18 expression, and LTB$_4$ production. The 16-HETE agonists have the following general structure:

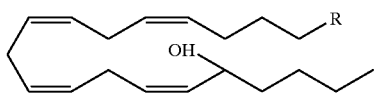

As used herein a "16-HETE antagonist" is a molecule encompassed by the above formulas wherein when either R$_1$ or R$_2$ is a C$_3$ alkyl the other is not a hydrogen. The modification at the OH group is sufficient to alter the biological activity of the molecules from an agonist to an antagonist. The 16-HETE antagonists inhibit 16-HETE activity and therefore prevent the 16-HETE induced inhibition of neutrophil aggregation and adhesion. An effective amount of a 16-HETE antagonist for preventing the inhibition of neutrophil adhesion/aggregation can be determined in the same assays described above in relation to 16-HETE agonists except that the antagonist may be added in conjunction with 16-HETE to determine if it inhibits or prevents 16-HETE activity. The 16-HETE antagonists have the following general structure:

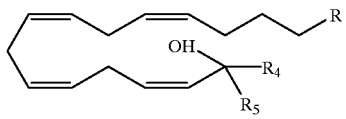

wherein R$_4$ and R$_5$ each independently is selected from the group consisting of hydrogen, C$_{1-2}$ alkyl, C$_{4-6}$ alkyl, alkenyl, alkynyl, alkoxy, aryl, and heteroaryl and wherein when either R$_1$ or R$_2$ is a C$_3$ alkyl the other is not a hydrogen.

The present invention thus involves methods and products for inhibiting neutrophil adhesion and neutrophil aggregation. One method of the invention involves administering 16-HETE agonist to neutrophils in situ in an amount effective to inhibit neutrophil aggregation and neutrophil adhesion. By definition, the word "in-situ" encompasses and includes the terms "in-vivo", "ex-vivo" and "in-vitro."

The invention includes compositions as well as methods for treating a subject to inhibit neutrophil adhesion or neutrophil aggregation by administering a 16-HETE agonist to a subject having an adverse medical condition mediated by neutrophil adhesion and/or neutrophil aggregation. In one embodiment a subject having an adverse medical condition mediated by neutrophil adhesion and/or neutrophil aggregation is one who has an inflammatory disease or is at risk of developing an inflammatory disease. In another embodiment a subject having an adverse medical condition mediated by neutrophil adhesion and/or neutrophil aggregation is one who has an ischemic disease.

A "subject" as used herein includes humans, non-human primates, dogs, cats, horses, sheep, goats, cows, rabbits, pigs and rodents.

Both inflammatory diseases and ischemic diseases are characterized by inflammation associated with neutrophil adhesion and neutrophil aggregation due to excessive neutrophil stimulation. While not intending to be bound by any particular theory, it is believed that excessive stimulation of neutrophils causes the neutrophils to migrate to the site of injury, where they release toxic factors and damage surrounding tissue. When the inflammatory disease is an acute stroke a tissue which is often damaged by neutrophil stimulation is the brain. As the active neutrophils accumulate in the brain an infarct develops.

An "inflammatory disease or condition" as used herein refers to any condition characterized by local inflammation at a site of injury or infection and includes autoimmune diseases, certain forms of infectious inflammatory states, undesirable neutrophil activity characteristic of organ transplants or other implants and virtually any other condition characterized by unwanted neutrophil activation. These conditions include but are not limited to meningitis, cerebral edema, arthritis, nephritis, adult respiratory distress syndrome, pancreatitis, myositis, neuritis, connective tissue diseases, phlebitis, arteritis, vasculitis, allergy, anaphylaxis, ehrlichiosis, gout, organ transplants and/or ulcerative colitis.

An "ischemic disease or condition" as used herein refers to a condition characterized by local inflammation resulting from an interruption in the blood supply to a tissue due to a blockage or hemorrhage of the blood vessel responsible for supplying blood to the tissue such as is seen for myocardial or cerebral infarction. A cerebral ischemic attack or cerebral ischemia is a form of ischemic condition in which the blood supply to the brain is blocked. This interruption in the blood supply to the brain may result from a variety of causes, including an intrinsic blockage or occlusion of the blood vessel itself, a remotely originated source of occlusion, decreased perfusion pressure or increased blood viscosity resulting in inadequate cerebral blood flow, or a ruptured blood vessel in the subarachnoid space or intracerebral tissue.

The methods of the invention are particularly preferred for treating cerebral ischemia. Cerebral ischemia may result in either transient or permanent deficits and the seriousness of the neurological damage in a patient who has experienced cerebral ischemia depends on the intensity and duration of the ischemic event. A transient ischemic attack is one in which the blood flow to the brain is interrupted only briefly and causes temporary neurological deficits, which often are clear in less than 24 hours. Symptoms of TIA include numbness or weakness of face or limbs, loss of the ability to speak clearly and/or to understand the speech of others, a loss of vision or dimness of vision, and a feeling of dizziness. Permanent cerebral ischemic attacks, also called stroke, are caused by a longer interruption in blood flow to the brain resulting from either a thromboembolism or hemorrhage. A stroke causes a loss of neurons typically resulting in a neurologic deficit that may improve but that does not entirely resolve. Thromboembolic stroke is due to the occlusion of an extracranial or intracranial blood vessel by a thrombus or embolus. Because it is often difficult to discern whether a stroke is caused by a thrombosis or an embolism, the term "thromboembolism" is used to cover strokes caused by either of these mechanisms. The term thromboembolism will be used throughout this patent application to describe thrombotic and embolic strokes. Hemorrhagic stroke is caused by the rupture of a blood vessel in a subarachnoid space or intracerebral tissue.

A preferred method of the invention involves the in vivo treatment of thromboembolic stroke by administering to a subject experiencing an acute thromboembolic stroke a 16-HETE agonist in an amount effective to reduce brain injury which would otherwise occur as a result of the stroke. The 16-HETE agonist may be administered to the subject in combination with other therapeutics for treating acute stroke. Preferably the 16-HETE agonist is administered in combination with a thrombolytic agent such as tPA.

The methods of the invention require the administration of the 16-HETE agonist in effective amounts. An effective amount of a 16-HETE agonist is one which inhibits to any degree neutrophil adhesion and neutrophil aggregation. An effective amount may be determined using the assay described in Example 3 infra for neutrophil adhesion. When the 16-HETE agonist is administered in combination with a thrombolytic agent such as tPA for the treatment of thromboembolic stroke an effective amount is one sufficient to reduce in vivo brain injury resulting from the stroke. A reduction of brain injury is any prevention of injury to the brain which otherwise would have occurred in a subject experiencing a thromboembolic stroke absent the treatment of the invention. Several physiological parameters may be used to assess reduction of brain injury, including smaller infarct size, improved regional cerebral blood flow, and decreased intracranial pressure, for example, as compared to pretreatment patient parameters, untreated stroke patients or stroke patients treated with thrombolytic agents alone.

Effective amounts will depend, of course, on the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment, particularly if acute thromboembolic stroke is the dominant clinical manifestation.

Both the dosage and time of administration of the 16-HETE agonist and the thrombolytic agent vary depending on a number of conditions. Acute stroke is an urgent medical condition with a small therapeutic window of time (possibly as brief as 6 hours) in which treatment is beneficial. Clot lysing drugs are believed most useful if administered during this window of time in order to at least partially restore cerebral blood flow within the compromised region and to sustain neuronal viability. Therefore, when the thromboembolic stroke is an acute stroke it is important that the thrombolytic agent be administered during the critical window of time. The dosage and time of administration of the thrombolytic agent also can be based on the target blood plasma level of the thrombolytic agent. Target plasma levels for humans of the thrombolytic agents are well known in the art. Studies involving these compounds at various dosages have been described and include Sherman D. G. et al, *Chest*, v. 102, p. 529S–537S; Albers, G. W., *Amer. J. Card.*, v. 75, p.34B–38B; and Saltiel and Ward, *Drugs*, v. 34, p. 222–262 (1987) all of which are hereby incorporated by reference. The time of the administration of 16-HETE agonist will also vary depending on patient parameters. Generally it is most effective to begin treatment as soon as possible after the start of the stroke.

It is expected that intravenous doses of the 16-HETE agonist in the range of 0.1 to 20 mg/kg/minute, in one or several administrations, will yield the desired results. A preferred daily dosage of 16(R)-HETE agonist is 1.0 mg/kg/minute. It is expected that intravenous doses of tPA in the range of 0.05 to 1.5 mg/kg, in one or several administrations, will yield the desired results. A preferred dosage of tPA is 0.9–1.1 mg/kg. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

The present invention also includes a pharmaceutical composition having a therapeutically effective amount of 16-HETE analog included in a pharmaceutically acceptable carrier. The term "pharmaceutically acceptable carrier" as used herein means one or more compatible solid or liquid filler, dilutants or encapsulating substances which are suitable for administration to a human or other animal. The term "carrier" denotes an organic or inorganic ingredient, natural or synthetic, with which the active ingredient is combined to facilitate the application. The components of the pharmaceutical compositions also are capable of being commingled with 16-HETE analog and with each other, in a manner such that there is no interaction which would substantially impair the desired pharmaceutical efficacy.

The pharmaceutical preparation of the invention includes a 16-HETE analog and a pharmaceutically acceptable carrier. In one embodiment, the 16-HETE analog is a synthetic preparation of 16-HETE analog. As used herein "a synthetic preparation of 16-HETE analog" includes a preparation of 16-HETE analog that is chemically derived. The chemically derived 16-HETE analog may be made by any chemical procedure known in the art. An example of a procedure used to synthesize 16-HETE analog is provided in Example 7. The compounds useful in the practice of the invention can be prepared in accordance with the reaction described in Example 7 below or through modifications thereof, that will be readily apparent to those skilled in the art. A suitable protocol can be selected with due consideration of the particular R, $R_1$, or $R_2$ substituent, commercial availability of some starting materials, and the like.

According to yet another embodiment, the 16-HETE analog is selected from the group consisting of 16(R)-HETE analog and 16(S)-HETE analog. As used herein "16(R)-HETE analog" is an analog of the R-stereoisomer of 16-hydroxyeicosatetraenoic acid. As used herein "16(S)-HETE analog" is an analog of the S-stereoisomer of 16-hydroxyeicosatetraenoic acid.

The pharmaceutical preparation of a 16-HETE agonist may be used alone or in combination with a therapeutic agent for treating an inflammatory disease or condition. Known therapeutics for treating an inflammatory disease or condition are described in medical textbooks such as Harrisons, Principles of Internal Medicine (McGraw Hill, Inc., New York). The particular therapeutic used depends on the nature of the disease or condition being treated.

Therapeutics useful in the treatment of inflammatory diseases or conditions involving infectious agents include various antipathogen agents, i.e., antibiotics, antivirals, antifungals and antiparasitics. The type and concentration of therapeutic depends inter alia on the infectious agent causing the inflammatory disease or condition. For example, chloramphenicol is therapeutically useful for the treatment of meningitis due to *Strepotococcus pneumoniae, Haemophilus influenzae,* and *Neisseria meningitides* but not in the treatment of meningitis due to *E. coli* or *Klebsiella pneumoniae.* Cefotaxime, ceftizoxime, ceftriaxone, ceftazidime, and moxalactam are useful in treating all forms of meningitis. Penicillin may also be used to treat *S. pneumoniae* and *N. meningitides.*

In general, therapeutics from the group comprising antibiotics include, for example, tetracycline antibiotics, such as chlortetracycline, oxytetracycline, tetracycline, demethylchlortetracycline, metacyclinc, doxycycline, minocycline and rolitetracycline; aminoglysodes, such as kanamycin, amikacin, gentamicin $C_{1a}$, $C_2$, $C_{2b}$ or $C_1$, sisomicin, netilmicin, spectinomycin, streptomycin, tobramycin, neomycin B, dibekacin and kanendomycin; macrolides, such as maridomycin and erythromycin; lincomycins, such as clindamycine and lincomycin; penicillanic acid (6-APA)- and cephalosporanic acid (7-ACA)-derivatives having (6β- or 7β-acylamino groups, respectively, which are present in fermentatively, semi-synthetically or totally synthetically obtainable 6β-acylaminopenicillanic acid or 7β-acylaminocephalosporanic acid derivatives and/or 7β-acylaminocephalosporanic acid derivatives that are modified in the 3-position, such as penicillanic acid derivatives that have become known under the names penicillin G or V, such as phenethicillin, propicillin, nafcillin, oxycillin, cloxacillin, dicloxacillin, flucloxacillin, cyclacillin, epicillin, mecillinam, methicillin, azlocillin, sulbenicillin, ticarcillin, mezlocillin, piperacillin, carindacillin, azidocillin or ciclacillin, and cephalosporin derivatives that have become known under the names cefaclor, cefuroxime, cefazlur, cephacetrile, cefazolin, cephalexin, cefadroxil, cephaloglycin, cefoxitin, cephaloridine, cefsulodin, cefotiam, ceftazidine, cefonicid, cefotaxime, cefinenoxime, ceftizoxime, cephalothin, cephradine, cefamandol, cephanone, cephapirin, cefroxadin, cefatrizine, cefazedone, ceftrixon and ceforanid; and other β-lactam antibiotics of the clavam, penem and carbapenen type, such as moxalactam, clavulanic acid, nocardicine A, sulbactam, aztreonam and thienamycin; and antibiotics of the bicozamycin, novobiocin, chloramphenicol or thiamphenicol, rifampicin, fosfomycin, colistin and vancomycin.

Anti-virals include Zidovudine (AZT-Retrovir), Zalcitabine (Hivid-ddC), Dicanosine (Videx-ddI), Protease inhibitors of retroviruses, integrase inhibitors of retroviruses and others well known to those skilled in the art.

Other therapeutics useful in the treatment of inflammatory diseases or conditions include, but are not limited to, anti-inflammatory agents, or antiphlogistics. Antiphlogistics are, for example, glucocorticoids, such as, cortisone, hydrocortisone, prednisone, prednisolone, fluorcortolone, triamcinolone, methylprednisolone, prednylidene, paramethasone, dexamethasone, betamethasone, beclomethasone, fluprednylidene, desoxymethasone, fluocinolone, flumethasone, diflucortolone, clocortolone, clobetasol and fluocortin butyl ester; immunosuppressive agents; penicillamine; hydroxychloroquine; and nonsteroidal inflammation-inhibitors (NSAID) which encompass anti-inflammatory, analgesic, and antipyretic drugs such as salicyclic acid, difunisal and from the group comprising substituted phenylacetic acid salts or 2phenylpropionic acid salts, such as alclofenac, ibufenac, ibuprofen, clindanac, fenclorac, ketoprofen, fenoprofen, indoprofen, fenclofenac, diclofenac, flurbiprofen, pirprofen, naproxen, benoxaprofen, carprofen and cicloprofen; oxicam derivatives, such as piroxicam; anthranilic acid derivatives, such as mefenamic acid, flufenamic acid, tolfenamic acid and meclofenamic acid; anilino-substituted nicotinic acid derivatives, such as the fenamates miflumic acid, clonixin and flunixin; heteroarylacetic acids wherein heteroaryl is a 2-indol-3-yl or pyrrol-2-yl group, such as indomethacin, oxmetacin, intrazol, acemetazin, cinmetacin, zomepirac, tolmetin, colpirac and tiaprofenic acid; idenylacetic acid of the sulindac type; analgesically active heteroaryloxyacetic acids, such as benzadac; phenylbutazone; etodolac; and nabumetone.

Other therapeutics useful in the treatment of inflammatory diseases or conditions include antioxidants. Antioxidants may be natural or synthetic. Antioxidants are, for example, superoxide dismutase (SUD), 21aminosteroids/aminochromans, vitamin C or E, etc. Many other antioxidants are well known to those of skill in the art.

The pharmaceutical preparation of the 16-HETE agonist also may be used alone or in combination with a therapeutic agent for treating an ischemic disease or condition. Therapeutics for treating ischemic diseases or conditions are described in medical textbooks such as Harrisons, Principles of Internal Medicine (McGraw Hill, Inc., New York ). The particular therapeutic used depends on the nature of the disease or condition. Examples of therapeutics useful in the treatment of ischemic diseases or conditions include anticoagulation agents, antiplatelet agents, and thrombolytic agents.

Anticoagulation agents prevent the coagulation of blood components and thus prevent clot formation. Anticoagulants include, but are not limited to, heparin, warfarin, coumadin, dicumarol, phenprocoumon, acenocoumarol, ethyl biscoumacetate, and indandione derivatives.

Antiplatelet agents inhibit platelet aggregation and are often used to prevent thromboembolic stroke in patients who have experienced a transient ischemic attack or stroke. Antiplatelet agents include, but are not limited to, aspirin, thienopyridine derivatives such as ticlopodine and clopidogrel, dipyridamole and sulfinpyrazone, as well as RGD mimetics and also antitlirombin agents such as, but not limited to, hirudin.

Preferably the 16-HETE agonist is administered in conjunction with a thrombolytic agent when treating an ischemic disease. Thrombolytic agents lyse clots which cause the thromboembolic stroke. Thrombolytic agents have been used in the treatment of acute venous thromboembolism and pulmonary emboli and are well known in the art (e.g. see Hennevekens et al, *J Am Coll Cardiol;* v. 25 (7 supp), p. 18S–22S (1995); Holmes, et al, *J Am Coll Cardiol;* v.25 (7 suppl), p. 10S–17S(1995)). Thrombolytic agents include, but are not limited to, plasminogen, $a_2$-antiplasmin, streptokinase, antistreplase, tissue plasminogen activator (tPA), and urokinase.

In a preferred embodiment of the invention tPA is the thrombolytic agent. The mature tPA polypeptide has 527 amino acids, at least 17 (Asn) of which have been shown to be linked with carbohydrate structures. Spellman et al., have identified several of these carbohydrates, including a high-mannose structure on amino acid 117, and di-tri-and tetra-antennary N-acetyllactosamine-type structures on amino acids 184 and 448 [*J. Biol. Chem.* 264 (24) 14100–14111 (1989)].

"tPA" as used herein includes native tPA and recombinant tPA, as well as modified forms of tPA that retain the enzymatic or fibrinolytic activities of native tPA. The enzymatic activity of tPA can be measured by assessing the ability of the molecule to convert plasminogen to plasmin. The fibrinolytic activity of tPA may be determined by any in vitro clot lysis activity known in the art, such as the purified clot lysis assay described by Carlson, et. al., *Anal. Biochem.* 168, 428–435 (1988) and its modified form described by Bennett, W. F. Et al., 1991, *Supra,* the entire contents of which are hereby incorporated by reference.

Recombinant tPA has been described extensively in the prior art. Several forms of recombinant tPA are commercially available such as ACTIVASE®.

Modified forms of tPA ("modified tPA") have been characterized and are known to those skilled in the art. Modified tPA includes, but is not limited to, variants having deleted or substituted amino acids or domains, variants conjugated to other molecules, and variants having modified glycosylation. Several preferred modified tPAs have been described in PCT Publication No. W093/24635; EP 352,119; EP382174; and Suzuki et al., *J. Cardiovasc. Pharmacal.* 22, 834–840 (1993). Each of these references is hereby incorporated by reference.

Briefly, PCT Publication No. W093/24635 discloses tPA variants having an extra glycosylation site at any of the amino acid positions 103–105 and the native glycosylation site removed at position 117 of the native human tPA. The amino acid number refers to the amino acid in that position of the mature, wild-type tPA polypeptide as disclosed in U.S. Pat. No. 4,766,075. These variants have extended circulatory half lives and exhibit substantially the same or improved fibrin binding affinity and fibrinolytic potency as compared to wild-type human tPA. The disclosed variants may also include at least one amino acid substituted in the 296–299 position with alanine and/or a substitution of the amino acids at positions 274–277 of wild type tPA (phenylalanine, arginine, isoleucine, lysine) with leucine, histidine, serine, and threonine, respectively. One particularly effective type of variant disclosed in the reference is a triple mutant variant of wild type tPA. The first mutation in a triple mutant is the addition of one glycosylation site at least one of the amino acid positions 103–105 by e.g., substituting the native amino acid sequence 103 with an asparagine as part of an Asn-X-Ser or Asn-X-Thr tripeptidyl sequence, wherein X is any amino acid except proline. The second mutation involves the removal of a glycosylation site at native amino acid site 117 (Asn) and replacing it with another amino acid, preferably glutamine. The third mutation is the replacement of native amino acids 296–302 with other amino acids. The most effective of the triple mutant variants is the specific molecule, T103N, N117Q, KHRR (296–299) AAAA tPA (TNK tPA).

EP 352,119 discloses Vampire Bat tPA's (Bat-Pa (H), (I), and (L)). Vampire bat-Pa's are variants of native tPA having a variety of sequence modifications. Although the Bat-Pa variants are structurally distinct from tPA because they lack the Kringle 2 domain and plasmin-sensitive processing site, these variants are functionally similar to native tPA. They are however, more potent than native tPA.

Suzuki et al., *J. Cardiovasc. Pharmacal.* 22, 834–840 (1993) disclose tPA variants in which a cysteine at position 84 of the growth factor domain of native tPA is replaced by scrine (C84S tPA). Although this variant retains the functional activity of native tPA, it has been shown to have a longer in vivo half life than native tPA.

The 16-HETE agonist may be administered alone or may be delivered in a mixture with other drugs, such as those disclosed above, for treating the inflammatory or ischemic disease or condition. In some embodiments, a common administration vehicle (e.g., pill, tablet, implant, injectable solution, etc.) would contain both the 16-HETE agonist useful in this invention and the therapeutic for treating the inflammatory or ischemic disease or condition. Thus, the present invention also provides pharmaceutical compositions, for medical use, which comprise the 16-HETE agonist of the invention together with one or more pharmaceutically acceptable carriers thereof and optionally other therapeutic ingredients.

The invention also includes compositions and methods for treating a subject to prevent 16-HETE inhibition of neutrophil adhesion or neutrophil aggregation and is therefore useful for immunostimulation by promoting neutrophil activity at sites of infection.

In addition to the therapeutic uses of the 16-HETE analogs, these compounds are also useful for a variety of in vitro purposes. For example, these compounds are useful in competition assays as well as intermediates or starting material for the synthesis of other compounds.

The invention also encompasses methods of inhibiting leukotriene production in a neutrophil by contacting the neutrophil with 16-HETE or a 16-HETE agonist. Leukotrienes are arachidonic acid metabolites having potent biological activity. The leukotrienes have been implicated in a variety of disease states including, for example, inflammation. Leukotriene $B_4$ is a potent chemotactic factor for inflammatory cells and has been found in the synovial fluids of rheumatoid arthritis patients and in psoriatic lesions. Leukotriene $C_4$ and $D_4$ have been demonstrated to be involved in constriction of human airway smooth muscle cells. The method of inhibiting leukotriene production in a neutrophil or in a subject having a condition mediated by leukotriene activity involves the step of administering a 16-HETE or an agonist thereof in an amount effective to inhibit leukotriene production. The leukotriene may be any type of leukotriene, but preferably is leukotriene $B_4$. A condition mediated by leukotriene activity is one selected from the group consisting of allergic rhinitis, adult respiratory distress syndrome, inflammatory bowel disease, ischemic induced myocardial injury, reperfusion injury, gout, asthma, psoriasis, stroke, spinal cord injury inflammation and traumatic brain injury. Preferably that disorder is an inflammatory disease. The treatment of diseases by promoting leukotriene production is described in U.S. Pat. No. 5,466,669 which is hereby incorporated by reference.

Methods for assessing leukotriene $B_4$ inhibition in neutrophils include the assay set forth below in Example 6. Many in vitro assays of leukotriene activity inhibition are also known in the art. These include for example, the rat and dog ex vivo leukotriene B4 inhibition assays set forth in U.S. Pat. No. 5,612,377 issued to Crooks et al., which is hereby incorporated by reference.

When administered, the formulations of the invention are applied in pharmaceutically acceptable amounts and in pharmaceutically acceptable compositions. Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1–2% W/V); citric acid and a salt (1–3% W/V); boric acid and a salt (0.5–2.5% W/V); and phosphoric acid and a salt (0.8–2% W/V).

Suitable preservatives include benzalkonium chloride (0.003–0.03% W/V); chlorobutanol (0.3–0.9% W/V); parabens (0.01–0.25% W/V) and thimerosal (0.004–0.02% W/V).

Generally, daily oral doses of active compounds will be from about 0.01 milligrams/kg per day to 1000 milligrams/kg per day. It is expected that oral doses in the range of 50 to 500 milligrams/kg, in one or several administrations per day, will yield the desired results. Dosage may be adjusted appropriately to achieve desired drug levels, local or systemic, depending upon the mode of administration. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

A variety of administration routes are available. The particular mode selected will depend, of course, upon the particular combination of drugs selected, the severity of the condition mediated by neutrophil adhesion and/or neutrophil aggregation being treated, the condition of the patient, and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, topical, nasal, direct injection, transdermal, sublingual or other parenteral routes. The term "parenteral" includes subcutaneous, intravenous, intramuscular, or infusion. Intravenous and intramuscular routes are not particularly suited for long term therapy and prophylaxis. They could, however, be preferred in emergency situations such as a stroke or myocardial infarction. Direct injection could also be preferred for local delivery to the site of injury. Oral administration may be preferred for prophylactic treatment because of the convenience to the patient as well as the dosing schedule.

The compositions may conveniently be presented in unit dosage form and may be prepared by any of the methods well known in the art of pharmacy. All methods include the step of bringing the 16-HETE analog into association with a carrier which constitutes one or more accessory ingredients. In general, the compositions are prepared by uniformly and intimately bringing the 16-HETE analog into association with a liquid carrier, a finely divided solid carrier, or both, and then, if necessary, shaping the product.

Compositions suitable for parenteral administration conveniently comprise a sterile aqueous preparation of the 16-HETE analog, which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for oral, subcutaneous, intravenous, intramuscular, etc. can be found in Remington's Pharmaceutical Sciences, Mack Publishing Company, Easton, Pa.

Compositions suitable for oral administration may be presented as discrete units such as capsules, cachets, tablets, or lozenges, each containing a predetermined amount of the 16-HETE analog. Other compositions include suspensions in aqueous liquors or non-aqueous liquids such as a syrup, an elixir, or an emulsion.

The 16-HETE agonist and thrombolytic agent or other therapeutic useful in the treatment of inflammatory or ischemic diseases may be administered by the same method, e.g. intravenous, oral, etc. or may be administered separately by different modes, e.g. 16-HETE agonist administered orally, thrombolytic agent administered intravenously, etc. In one embodiment of the invention the 16-HETE agonist and the thrombolytic agent or other therapeutic are co-administered intravenously. In another embodiment the 16-HETE agonist and the thrombolytic agent or other therapeutic are administered separately.

Other delivery systems can include time-release, delayed release or sustained release delivery systems. Such systems can avoid repeated administrations of the 16-HETE analog of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di- and tri-glycerides; liposomes; phospholipids; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic conditions mediated by neutrophil adhesion and/or neutrophil aggregation. "Long-term" release, as used herein, means that the implant is constructed and arranged to deliver therapeutic levels of the active ingredient for at least 7 days, and preferably 30–60 days. The implant may be positioned at the site of injury. Long-term sustained release implants are well known to those of ordinary skill in the art and include some of the release systems described above.

EXAMPLES

Example 1

Identification and Quantitative Analysis of Neutrophil Arachidonic Acid Metabolites Materials HETE standards (16(R)-, 16(S)-, 17-, 18-, 19- and 20-HETE) and 19-HETE-$d_3$ (99+atom % deuterium) were synthesized as described in Falck el al., J. Biol. Chem. 265, 10244–10249 (1990). The standard lipoxygenase-derived HETEs (5-, 8-, 11-, 12-, and 15-HETE) were obtained from Biomol. Thrombin and FMLP were purchased from Parke-Davis (Morris Plains, N.J.). All solvents used were HPLC grade (Burdick and Jackson, Muskegon, Mich.) and other reagents were of the highest grade commercially available. BSTFA was purchased from Aldrich and [1-$^{14}$C] arachidonic acid (55 mCi/mmol) was purchased from du Pont Corp. (Wilmington, Del.). All other reagents were purchased from Sigma Chemical Co., St. Louis, Mo. unless otherwise noted.

Methods

Preparation of Human Polymorphonuclear Leukocytes

Venous blood (60–70 ml) was collected from four healthy, normal volunteers into syringes containing heparin (1 U/ml). Polymorphonuclear leukocytes (PMNs) were isolated by a histopaque density gradient technique as previously described in Liu et al., *Adhesion, Its role in Inflammatory Disease,* Freeman and Co., New York, 1992, pp 189–192. Briefly, blood aliquots (6 ml) were layered over two layers (3 ml) of histopaque 1077 and 1119 in a conical centrifuge tube. The sample was then subjected to centrifugation at 100×g for 30 minutes at room temperature and the top layer, containing the neutrophils, was carefully collected. Hypotonic lysis was used to separate out the red blood cells. The neutrophils were then isolated from the sample by centrifugation (2000×g) and suspended in Haiks balanced salt solution (HBSS) containing 1 mM $Ca^{2+}$ and 0.8 mM $Mg^{2+}$ for studies involving arachidonic acid metabolism, and in M199 (with 1% BSA) for neutrophil adhesion assays. Total cells were counted using a hemocytometer and leukocytes were counted after staining with Wright-Giemsa stain. For each experiment, the cell preparations used contain$\geq$97% neutrophils, having$\geq$95% viability as determined by a trypan blue exclusion assay.

Arachidonic Acid Metabolism

Neutrophils were suspended in HBSS ($10^7$ cells per ml) and allowed to stand for 10 minutes. Radioactively labeled arachidonic acid (1 to 50 $\mu$M) was produced with either a $^{14}$C label containing 0.5 to 1 $\mu$Ci [1-$^{14}$C]arachidonic acid/1 to 50 $\mu$M unlabeled arachidonic acid] or a deuterium label (1 unit arachidonic acid-$d_8$/2 units unlabeled arachidonic acid). The experimental samples were preincubated with inhibitors [SKF 525A (100 $\mu$M) or BW755C (94 $\mu$M) or indomethacin (10 $\mu$M)] for 10 minutes prior to the addition of arachidonic acid. At the end of the incubation, the labeled arachidonic acid, was added to the neutrophil suspension and allowed to incubate for 10 minutes at 37° C. A control sample was not subjected to preincubation with inhibitors.

After ten minutes in arachidonic acid the reaction was terminated by the addition of cold methanol (four volumes). The neutrophil methanol mixture was then subjected to acidification at pH 3.5 to 4 and the metabolite fraction was extracted with ethyl acetate. The extracts were washed with water and dried over anhydrous sodium sulfate. The metabolites were further purified by filtration to remove the sodium sulfate and evaporation to remove the ethyl acetate. The resultant residue was dissolved in methanol and injected on a reverse phase HPLC column (ODS silica, 250×4.6 mm, Beckman). Eluate was collected at 1 ml/min. The solvent gradient was started at acetonitrile/water/acetic acid (62.5:37.5:0.1) and increased to 100% acetonitrile in 20 minutes. The effluent was passed through a UV detector (HP1050/ChemStation—Hewlett-Packard, Palo Alto, Calif.) and a radioactivity detector (Radiomatic, Meridian, Conn.) with a splitter (ratio 1:10) and collected in 1 ml fractions.

Gas Chromatography/Mass Spectrometry

The fractions containing radioactive metabolites were evaporated under vacuum and derivatized as follows before being subjected to mass spectrometric analyses: Methyl esters were prepared with diazomethane solution in ether (100 $\mu$l, 3 min); Pentaflurobenzyl esters (PFB) were prepared with pentafluorobenzyl bromide and N,N-diisopropylethylamine as described Balazy, *J. Biol. Chem.,* 266, 23561–23567 (1991); and Trimethylsilyl (TMS) ethers of hydroxyl groups were prepared with N,O-bis (trimethylsilyl) trifluoroacetamide (BSTFA). The derivatives were then dissolved in isooctane and analyzed by GC/MS as describe below. In some experiments, aliquots of isooctane solution were mixed with catalytic amounts of 5% rhodium on alumina (Aldrich, Milwaukee, Wis.) in a microvial and bubbled with hydrogen gas at 0° C. for 5 min Balazy and Murphy *Anal. Chem.* 58, 1098–1100 (1986). The catalyst was precipitated by centrifugation and the reduced derivative was analyzed by GC/MS.

Aliquots (1 µl) were injected into a 15 m fused silica GC column (DB-1, 0.25 mm i.d., 0.25 µm film thickness, J and W Scientific, Folsom, Calif.) and eluted with a flow of helium (44 cm/s) and with a temperature program from 170° C. to 300° C. (rate 15° C./min). The mass spectrometer was operated in chemical ionization mode with negative ion detection (electron capture) using methane as a reagent gas (2.6 torr source pressure) or in electron ionization mode at 70 eV. The relative retention time of each derivative was expressed as carbon number equivalent calculated from retention times obtained for a series of methyl or PFB esters of saturated fatty acids ($C_{14}$–$C_{24}$) as described (Balazy, supra).

Quantitative Analysis of 20-HETE and 16-HETE in Neutrophil Phospholipids

Suspensions of human neutrophils (0.5 to $0.9 \times 10^8$ cells per ml) from three healthy donors not receiving medication were extracted using the Bligh and Dyer procedure as described Zhu et al., *Hypertension* 25, 854–859 (1995). The neutrophil total lipids containing 0.1 to 0.3 µmol of phosphorus, were treated with 200 µl of 0.1 N potassium hydroxide/ethanol (1:1) or water/ethanol (in control experiments) for 1 hr at 50° C., and extracted with ethyl acetate after acidification (pH 3–4). Prior to extraction, internal standard, 19-HETE-$d_3$ (2 ng), was added. The extracts were dried and purified by RP-HPLC. Following derivatization with PFB bromide and BSTFA, the samples were analyzed by GC/MS as described (Zhu, supra). The amount of endogenous HETE was calculated from the standard curve prepared with 2 ng of 19-HETE-$d_3$ and 19-HETE (0.1 to 1 ng). The amount of phosphorus in the samples analyzed by GC/MS was determined spectrophotometrically (Zhu, supra).

Stereochemical Analysis of 16-HETE

The radiolabeled material in fraction 10, 16(R)-HETE, 16(S)-HETE and 20-HETE were separately esterified with pentafluorobenzyl bromide and the hydroxyl group was further esterified with a-naphthoyl chloride as described Laethem et al., *J. Biol. Chem.* 268, 12912–12918 (1993). The derivatives were purified by reverse-phase HPLC and analyzed on chiral-phase column (Pirkle type 1-A, 250×4.6 mm, Regis, Morton Grove, Ill.) and eluted with hexane containing 0.1% of isopropanol at 1 ml/min. The effluent was analyzed by a UV detector and collected in 0.2 ml fractions. The amount of radioactivity in these fractions was measured using scintillation counter.

Results

Identification of Neutrophil Arachidonic Acid Metabolites

Previously, Bednar et al. demonstrated that incubation of arachidonic acid with intact canine and human neutrophils produce polar metabolites whose formation can be inhibited by SKF525A or carbon monoxide (Bednar et al., *Biochem. Biophys. Res. Commun.* 123, 581–588 (1984); Bednar et al., *Biochem. Pharmacol.* 36, 1741–1747 (1987); and Kraemer, supra). These studies were later extended in human neutrophils. The latter studies revealed that intact neutrophils contain cytochrome P450 monooxygenase system and produce a cytochrome P450-dependent arachidonate metabolite which was found to inhibit neutrophil aggregation (Kraemer, supra, Bednar et al., *Biochem. Pharmacol.* 36. 1741, 1987). The work of Hatzelmann and Ullrich (Hatzelmann, supra) showed that intact human neutrophils metabolize arachidonic acid into two major compounds: 20-HETE, an omega-hydroxylase product, and 15-HETE, a lipoxygenase product. Surprisingly the inventors of the present invention found that neither 20-HETE nor 15-HETE inhibited neutrophil aggregation.

In order to identify the neutrophil arachidonic acid metabolites responsible for inhibiting neutrophil aggregation, human neutrophils were incubated with radiolabeled arachidonic acid. Incubations of arachidonic acid with human neutrophils resulted in formation of four radiolabeled products (metabolites A, B, C, and D). The major peak (D) contained unmodified arachidonic acid. Peaks B and C combined contained 5 to 8% of the total radioactivity injected and displayed absorbance at 234 nm, which is typical of conjugated double bonds. The material in peak A contained 10 to 15% of the radioactivity and it did not absorb UV light above 205 nm. Preincubation with inhibitors, established that the formation of product A by human neutrophils can be inhibited with SKF525A but not with BW755C suggesting that product A originated from metabolism mediated by cytochrome P450 monooxygenase, and not by lipoxygenase or cyclooxygenase.

Metabolite A was subjected to GC/MS analysis in order to further elucidate the components of metabolite A. The GC/MS analysis of metabolite A as a PFB, TMS derivative, with monitoring of ion m/z 391, which corresponded to a PFB ester, TMS ether derivative of a HETE molecule, produced an ion chromatogram which indicated the presence of two components at retention times of 7.33 min (component A1) and 8.01 min (component A2), having carbon number equivalents 20.9 and 22.4, respectively. Although variable amounts of metabolite A was isolated from neutrophils of each of the individual donors, the GC/MS analyses consistently yielded components A1 and A2 with a relative abundance of approximately 1 to 4. When deuterium-labeled arachidonic acid was included in the incubations, additional clromatographic peaks were observed (corresponding to ion m/z 399) which had retention times similar but slightly shorter than the non-labeled analogs, possibly as a result of the isotopic effect of the deuterium substitution.

The gas chromatographic mobility was compared with that of HETE standards. This comparison revealed that the component A2 coeluted with 20-HETE while the component A1, coeluted with 16-HETE. The PFB, TMS derivative of a standard sample of lipoxygenase HETEs (containing equal amount of 5-, 8-, 12-, and 15-HETE) eluted as a single peak at 7.45 min and did not coelute with either component of metabolite A or either of the 20- or 16-HETEs.

The electron capture spectra obtained for both the A1 and A2 components contained prominent ions at m/z 391 (M-181, loss of pentafluorobenzyl) and at m/z 301 (M-181-90, loss of pentafluorobenzyl and trimethylsilanol, $SiMe_3OH$) and were consistent with molecular weight of 320 amu for the metabolite having one hydroxyl group in the arachidonic acid structure. Inclusion of arachidonic acid-$d_8$ in the incubations produced a spectrum containing additional isotopic ion at m/z 399. When synthetic 16-HETE was mixed with metabolite A, only the intensity of component A1 increased and the added compound could not be separated from biologically derived A1, strongly indicating that Product A1 was 16-HETE. Catalytic reduction of PFB, TMS derivative resulted in a shift by 8 mass units producing a spectrum with ion m/z 399, typically observed for a HETE molecule with four double bonds reduced.

To further characterize these two components, the metabolite A was methylated, silylated with BSTFA and catalytically reduced with hydrogen. The electron ionization mass spectrometry of component A1 (carbon number equivalent 22.3) produced ions at m/z 399 (M-CH$_3$), m/z 357 and m/z 159 which originated from α-cleavage at C16, m/z 235 (m/z 357-32-90, loss of CH$_3$OH and SiMe$_3$OH). Fragment m/z 357 displayed a complex isotopic cluster of ions resulting from scrambling of deuterium during catalytic hydrogenation of isotopically-labeled molecule. Fragment ion m/z 328 originated from rearrangement of trimethylsilyl group to carboxylic group similar as observed for saturated hydroxy fatty acids. Eglinlon et al., *Org. Mass. Spectrom.* 1, 593–611 (1968). The spectrum of synthetic, reduced 16-HETE, revealed the presence of these ions at retention time equivalent to carbon number 22.3 and was similar to the spectrum published by Falck et al., supra.

The stereochemistry of the hydroxyl at C16 in component A1 was established by chiral phase HPLC. The mixing of metabolite A with racemic synthetic 16-HETE followed by derivatization into 16-naphthoyl, PFB ester resulted in separation of this derivative into enantiomers and revealed that the radioactivity from biologically derived compound coeluted with the R isomer. The 20-naphthoyl, PFB derivative of 20-HETE was completely separated from the 16-HETE derivative during RP-HPLC purification prior to chiral analysis. These data were consistent with the structure of metabolite A1 as 16(R)-hydroxy-5,8,11,14-eicosatetraenoic acid formed by the action of cytochrome P450 on arachidonic acid assuming that the configuration of double bonds was unchanged from that of arachidonic acid. The electron ionization of the reduced molecule of component A2 as methyl ester TMS derivative (carbon number equivalent 23.5) revealed ions at m/z 414 (M$^+$), m/z 399 (M-CH$_3$), m/z 367 (M-CH$_3$—CH$_3$OH), m/z 324 (M-SiMe$_3$OH), m/z 292( M-32-90, loss of CH$_3$OH and SiMe$_3$OH), m/z 146 (SiMe$_3$O(CH$_2$)$_3$),CH$_3$) m/z 103 (Me$_3$Si—O=CH$_2$). The isotopic cluster of ions m/z 399 and 367 resulted from the scrambling of deuterium-labeled molecule during catalytic reduction of double bonds. This spectrum was consistent with reduced methyl ester, TMS ether derivative of a mixture of 20-HETE and 20-HETE-d$_8$.

Electron ionization of reduced metabolite B as methyl ester, TMS ether produced a spectrum (carbon number equivalent 21.8) which contained prominent ions at m/z 414 (M$^+$), 399 (M-15), 343 (α-cleavage at C15) and a base peak at m/z 173 (SiMe$_3$OCH(CH$_2$)$_4$CH$_3$). Ion m/z 343 displayed distinct isotopic cluster as expected for a reduced deuterium-labeled molecule. It was concluded that the metabolite B was 15-HETE.

The material in metabolite C contained at least two components absorbing UV light at 234 nm. The latter eluting component coeluted with standard 5-HETE. The material in peak C produced a complex mass spectrum indicative of 5-HETE and another unidentified product. Longer incubations of arachidonic acid with human neutrophils also resulted in formation of a polar compound identified as 20-carboxy arachidonic acid which originated from oxidative metabolism of 20-HETE.

Therefore, the mass spectrometric analyses of arachidonic acid metabolites produced by intact human neutrophils obtained from three human donors, revealed that a single monitoring of ion m/z 391, corresponding to a PFB, TMS derivative of a HETE molecule, consistently showed a minor, less polar component in addition to 20-HETE. Using mass spectrometric analysis and chiral analysis, it was revealed that the minor component was 16(R)-HETE, a product of cytochrome P450 and arachidonic acid which has not been previously observed in human PMN. Although, two recent studies provided mass spectrometric characterization (Hatzelmann, supra) and quantitation of 20-HETE in human PMNs (Hill, supra), 16-HETE was not observed. The lack of detection of 16-HETE is most likely due to the similar chromatographic mobility of 20-HETE and 16-HETE during RP-HPLC which results in the inability to observe separate peaks for these two HETEs using a low resolution of the radioactivity detector. It was also found in the present study that gas chromatographic conditions were capable of fully separating derivatives of unreduced 20-HETE from four subterminal HETEs. These chromatographic conditions were different than those described for isolation of 20-HETE from human neutrophils (Hatzelmann, supra, Hill, supra).

Example 2

16-HETE and 20-HETE are Released from Neutrophil Phospholipids

Methods

Quantitative analysis of 20-HETE and 16-HETE in neutrolphilphospholipids was performed as described above in Example 1.

Results

Release of Endogenous 16-HETE and 20-HETE from Neutrophil Phospholipids

When total lipid extracts from intact neutrophils were purified by HPLC and analyzed by electron capture GC/MS, no HETE molecules were detected by this GC/MS assay and therefore must be less than 10 pg per 10$^8$ cells. However, when neutrophil lipids were hydrolyzed with 0.1 N potassium hydroxide, 20-HETE and 16-HETE were detected at a concentration of 341±69 pg per 10$^8$ cells and 108±26 pg per 10$^8$ cells respectively (Table 1).

TABLE 1

Amounts of 16-HETE and 20-HETE released from intact human neutrophil phospholipids following alkaline hydrolysis

|  | 16-HETE (pg/10$^8$ cells) | 20-HETE (pg/10$^8$ cells) |
| --- | --- | --- |
| control | n.d. | n.d. |
| Hydrolysis | 108 ± 26 | 341 ± 69 |

Average ± SEM of single measurements of neutrophil samples obtained from three donors.
HETEs were measured by gas chromatography/mass spectrometry with 19-HETE-d$_3$ as an internal standard as described in the methods above.

Example 3

16-HETE Inhibits Neutrophil Adhesion

Methods

Synthesis of 16-HETE

Nucleophilic S$_N$2 addition of butyl magnesium bromide in Et$_2$O to the acetalic center of homochiral 1,3-dioxolan-4-one, prepared from 3-methyl-2 -butenal and (R)-mandelic acid, followed by esterification with diazomethane readily afforded substituted O-allyl mandelate. Diisopropyl acetal was then obtained via low temperature ozonolysis, with Me$_2$S workup and incubation of the resultant crude aldchyde with triisopropyl orthoformate in the presence of catalytic pyridinium p-toluenesulfonate (PPTS). Mild oxidative decarboxylation via an in situ-generated dioxetanone led to the corresponding benzoate. Minor amounts of free alcohol released during this process were benzolylated and the combined degradation product was hydrolyzed, using trifluoracetic acid to furnish the aldehyde. Wittig condensation with 13-carbomethoxytrideca-3(Z), 6(Z), 9(Z)-trien-1-ylidene-triphenylphophorane and methanolysis of the benzoate produced methyl 16(S-OH-AA(8), $[\alpha]_D$=−5.4 (c 0.7, acetone). Mitsunobu inversion ($PhCO_2H, Ph_3P$, DEAD) and benozate removal (NaOMe, MeOH, 24° C., 2h) yielded the 16(R)-isomer.

Neutrophil Adhesion

Isolated neutrophils were resuspended in M199 containing 1% BSA with a final concentration of $3\times10^6$ cells per ml. Cells suspensions (1 ml) were incubated with or without a test compound, 16(S)-HETE, 16(R)-HETE, or 20-HETE (concentrations 0.01 to 10 μM) for 10 min and then placed into gelatin-coated wells and further incubated for 20 min at 37° C. The wells were washed three times with 0.5 ml of solution M199 to remove non-adherent cells. The adherent cells were then removed by addition of 0.4 ml of 0.25% trypsin-EDTA in 0.1 M PBS to the gelatin-coated wells and incubation for 10 min at 37° C. The incubates were transferred and the wells were washed with 0.1 ml of M199 solution. The amount of cells in combined solutions was counted. In some experiments, the adhesion of neutrophils was stimulated by addition of 1 U/ml of thrombin to neutrophil suspension immediately prior to the transfer of cells to the wells. Experiments were performed in duplicates for each concentration of HETE. The inhibition of adhesion was expressed as percent of cells remaining in suspension (non-adherent) relative to control. The range of adherent PMNs in control incubations was 6 to 23%. This was increased two-fold in the presence of thrombin.

Neutrophil Aggregation and Chemiluminescence

Stimulated neutrophil aggregation and oxygen free radical release were examined in whole human blood using a whole-blood aggregometer-chemiluminometer (Chronolog, Haverton, Pa.) as described in Bednar et al. *J. Thromb. Thrombol.* 1, 179–185 (1995). Briefly, blood samples containing heparin (1 U/ml) as the anticoagulant were diluted in HBSS in proportion 1 to 9. Diluted blood aliquots (1 ml) were stirred (400 rpm) in a prewarmed (37° C.) siliconized cuvette containing cytochalasin b (5 μg/ml) and luminol (in 8 μl DMSO, 500 μM final concentration) and the test HETE (concentration 0.01 to 10 μM) for 10 min. Neutrophils were stimulated with a submaximal dose of fMLP ($5\times10^{-7}$M final concentration). The aggregation and chemiluminescence were simultaneously measured as changes of impedance and luminescence, respectively. The fMLP-induced chemiluminescence was calculated as the peak height of the reaction.

Results

Neutrophil-inhibitory Activity of 16-HETE

Figure 2:
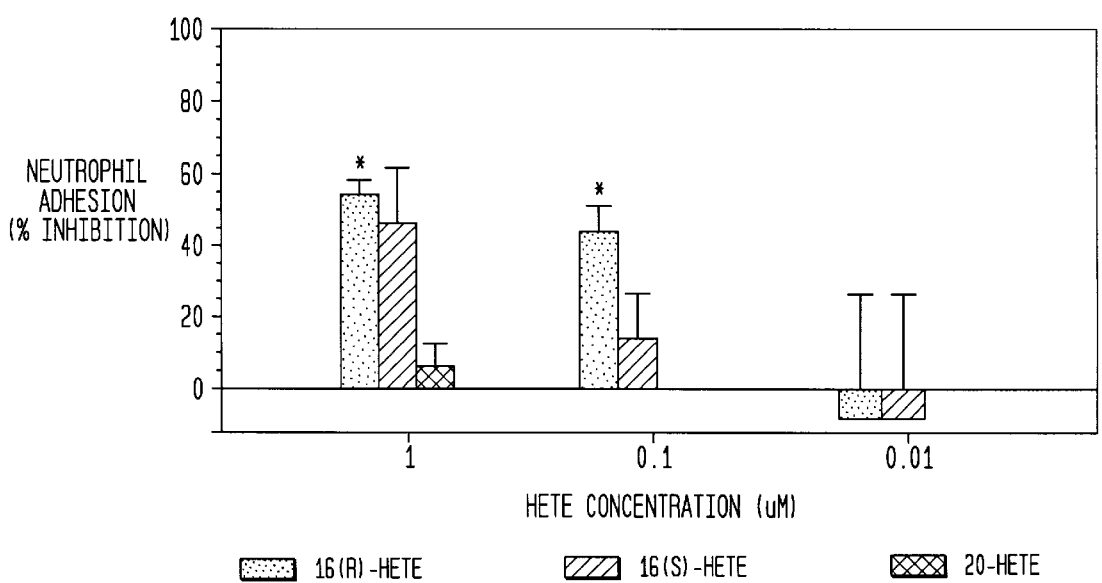
FIG. 2 is a bar graph depicting the percent inhibition of neutrophil adhesion to a gelatin matrix in response to a 10 minute pre-incubation with 16(R)-HETE, 16(S)-HETE, and 20-HETE on thrombin-stimulated human neutrophils.

In order to determine the biological effects of 16-HETE on human neutrophils, neutrophil adhesion was analyzed after preincubation of 16-HETE and 20-HETE. At concentrations≦20 μM, 16-HETE (R or S) and 20-HETE had no detectable agonist activity on human neutrophils. However, both stereoisomers of 16-HETE inhibited basal (FIG. 1) and thrombin-stimulated (FIG. 2) neutrophil adhesion to gelatin matrix. Treatment of neutrophils with 16(R)-HETE or 16(S)-HETE at concentrations from $10^{-8}$ to $10^{-5}$M inhibited neutrophil adhesion in a dose-dependent maimer. The 16(R)-HETE at a concentration of 1 μM significantly (p<0.05) inhibited basal neutrophil adhesion by 73±11% and thrombin-stimulated adhesion (1 U/ml, $3\times10^6$ cells/ml) by 50±4%. In contrast to the 16(R)-HETE, the 16(S)-HETE was less potent in inhibiting unstimulated (39±8%) and thrombin-stimulated (40±14% inhibition) neutrophil adhesion at a concentration of 1 μM, although it exhibited the same biological activity as 16(R)-HETE. Preincubation of neutrophils with 10 μM of 16(R)-HETE completely inhibited neutrophil adhesion to gelatin. 20-HETE at concentrations ≦10 μM did not inhibit neutrophil adhesion under either basal or stimulated conditions.

The 16(R)-HETE also inhibited fMLP-induced neutrophil aggregation (Table 2) with $IC_{50}$ of 1.2 μM. The 16(S)-HETE and 20-HETE were not active at concentrations of ≦10 μM. Finally, the fMLP-stimulated release of oxygen free radicals was not inhibited by any of the three HETEs tested at concentrations≦10 μM (Table 2).

The effect of preincubation with 16(R)-HETE, 16(S)-HETE and 20-HETE on neutrophil aggregation and oxygen free radicals (OFR) release stimulated by fMLP ($5 \times 10^{-7}$M, final concentration) in diluted human blood

|  | Aggregation | OFR Release |
| --- | --- | --- |
| 16(R)-HETE | 42.0 ± 11.0* | 8.9 ± 5.1 |
| 16(S)-HETE | 7.0 ± 3.5 | 5.6 ± 16.7 |
| 20-HETE | 8.1 ± 2.6 | 3.9 ± 13.4 |

Values represent percent of inhibition from HETE untreated cells (N = 3 to 4 in each group). 1 mM concentrations of HETE was used for each analysis. OFR release was measured by chemiluminescence as described above.
*(p < 0.05)

The biological effects of 16-HETE on human neutrophils have not been previously reported. 16(R)-HETE displayed a potent inhibitory activity towards unstimulated and stimulated neutrophils. The biological effect observed with 16(R)-HETE was more potent than the effect observed with the other stereoisomer, 16(S)-HETE. 16(R)-HETE inhibited neutrophil adhesion, basal and thrombin-stimulated, and fMLP-induced neutrophil aggregation.

It was observed that in order to inhibit the adhesion of neutrophils to a gelatin matrix, a 10 min preincubation with 16(R)-HETE was required. This could reflect the time necessary for the 16-HETE to achieve membrane concentration sufficient for inhibition of adhesion. While not intending to be bound by any particular theory, the data presented above suggest that 16-HETE inhibits neutrophil activation indirectly, through induction of changes in phospholipid membrane, possibly via incorporation into sn-2 position of lyso-phospholipids. The results presented here clearly demonstrate that neutrophil lipids contain detectable quantities of 16-HETE and 20-HETE which must originate from endogenous arachidonic acid and exist as preformed cellular components in a form sensitive to alkaline hydrolysis.

In summary we have shown that 16(R)-HETE is formed in human neutrophils from arachidonic acid, it is an endogenous compound, and it has potent anti-adhesion and anti-aggregatory properties. These observations indicate that 16-HETE is an important effector in regulating the physiological response to human neutrophil activation.

Example 4

Intravenous Administration of 16-HETE in Combination with tPA is More Effective than tPA in Reducing Brain Injury in a Rabbit Model of Thromboembolic Stroke Methods New Zealand rabbits of either sex, weighing 3–4 kilograms were used for the study. Prior to the start of the experiment, the rabbits were divided into three groups, those that were administered both 16-HETE at a rate of 1 mg/kg per minute for one hour and tPA (Genentech, Inc., San Francisco, Calif.) at a concentration of 6.3 mg/kg, tPA alone, or vehicle.

On the day of treatment the animals were fasted for 12 hours with free access to water and then anesthetized with an intramuscular solution of ketamine (50 mg/kg), acepromazine (20 mg) and xylazine (5 mg/kg). This solution was subsequently used to maintain a surgical depth of anesthesia as determined by responses to various physiologic and autonomic stimuli, including mean arterial pressure and response to paw pinch.

The animals were prepared for surgery by introducing femoral venous and arterial catheters (PE50 and 90, respectively; Clay Adams, Parsippany, N.J.). The catheters were placed for subsequent blood sampling, including blood gas and arterial pressure, drug infusions, and fluid replacement.

All animals were tracheotomized and mechanically ventilated in order to maintain arterial blood gases within a physiologic range. Arterial blood gas measurements (pH, $pCO_2$, $pO_2$) were determined, using a Corning 168 blood gas monitor. Arterial blood gases were maintained within physiologic range throughout the protocol with hematocrit and arterial pressure maintained near initial base line values.

A midline scalp incision was made to expose the calvarium. Bilateral craniectomies were performed in which a temperature sensor was placed in order to measure brain temperature and a 30-gauge platinum-iridium electrodes were inserted 2 mm within the cortical mantle to monitor regional cerebral blood flow via the hydrogen clearance technique. All the instrumentation was carefully fixed in place with fast-setting epoxy. Both core and brain temperatures are maintained within 1° C. of base line values through the use of heating blankets and heating lamps.

Once the surgical procedures had been prepared, the instrumentation was allowed to equilibrate for 30 minutes, prior to embolization.

A clot embolus was prepared 4 hours prior to the embolization procedure by mixing 1 cc of donor rabbit blood with 20 µM tin granules (50 mg tin/ml whole blood) and placed in PE 90 tubing pretreated with thrombin (Park-Davis, Morris Plains, N.J.).

One hour after embolization 16-HETE was continuously infused into the animals at a rate of 1 mg/kg per minute for 1 hour. The thrombolytic tPA was infused between 3 and 5 hours following embolization at a dose of 6.3 mg/kg. The animals received either 16-HETE, tPA, 16-HETE plus tPA, or vehicle. Measurements were taken for a total of 7 hours following clot embolization.

Following determination of all base line values, the right common carotid bifurcation is exposed, the internal carotid artery (ICA) isolated, a micro-arteriotomy performed and the 15-mm clot embolized intracranially via the ICA. ICA flow is then reestablished via a micro-arteriorrhaphy. Post embolization rCBF is then determined and the experiment continued if rCBF is reduced to 15 cc/100 gm/minute in at least one of the PT-IR electrodes within the embolized hemisphere. The value of rCBF reduction is based on historical studies demonstrating the intensity of ischemia necessary to produce irreversible brain injury, if no therapeutic intervention is instituted. A submental vertex X-ray, using a Phillips dental X-ray machine, verified intracranial placement of the tin-tagged clot. Submental vertex X-rays were repeated every 30 minutes until termination of the experiment. Care was taken to maintain the same position of the X-ray tube relative to the skull. Clot lysis was defined as complete dissolution of the embolus.

At the completion of the study the animals were euthanized, a calveroectomy was performed, and the brain was harvested. The brain was carefully inspected and X-rayed for the presence and position of a residual clot. The brain was then subjected to 2-mm coronal sectioning and incubated in isosmolar TTC at 37° C. for 30 minutes to delineate the region of infarct. Infarct size is determined according to the modification described by Lin et al., *Stroke*, 24:117–121, 1993. Each brain section was also examined for gross hemorrhage.

At the time of embolization, the common, external, and internal carotid arteries were all transiently excluded from the circulation and the clot embolus injected into the anterior circulation of the brain via the internal carotid artery. Immediately following clot embolization, regional cerebral blood flow was measured by the hydrogen clearance technique (Young W., *Stroke*, 11:552–564, 1980) within the embolized hemisphere in order to insure a reduction in regional cerebral blood flow to $\leq 15$ cc/100 g/min. Additionally, a submental vertex X-ray confirmed intracranial clot placement. All animals met both criteria. Internal carotid artery patency was restored using 10-0 interrupted nylon sutures (Sharpoint, Reading, Pa.).

Statistical analysis of all hematological variables, ex-vivo neutrophil function, cerebral blood flow, and infarct size was performed using repeated measures analysis of variance (ANOVA) to detect significant differences between groups and among time points.

Results

Hematocrit, arterial blood gases, and mean arterial pressure were monitored and controlled prior to and following clot embolization. These parameters, as well as core and brain temperature, were well maintained throughout the experimental protocol and generally showed no statistical significance in experimental vs. control groups.

Figure 3:
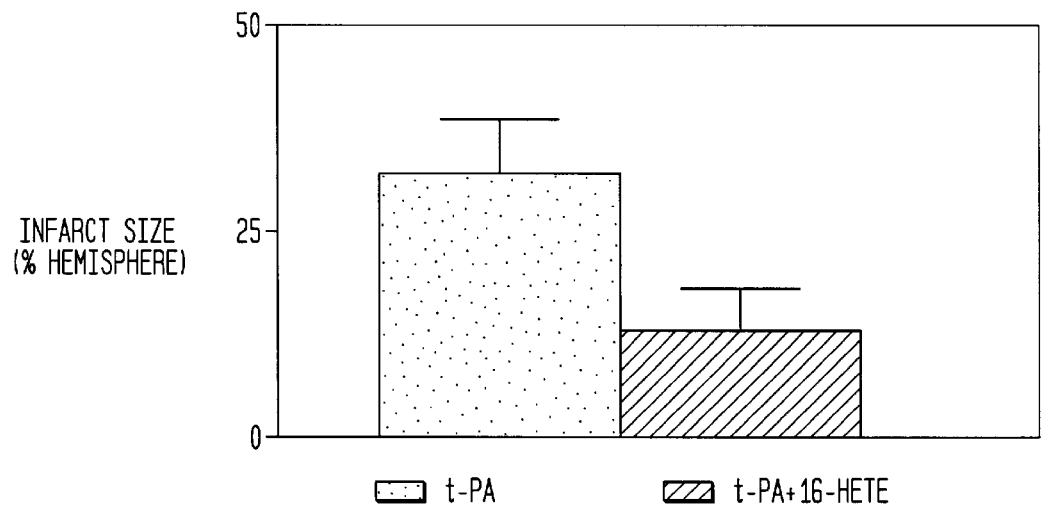
FIG. 3 is a bar graph depicting brain infarct size in a rabbit model of acute stroke, treated with either tPA alone (solid bar) or 16-HETE plus tPA (cross-hatched bar)
Figure 4:
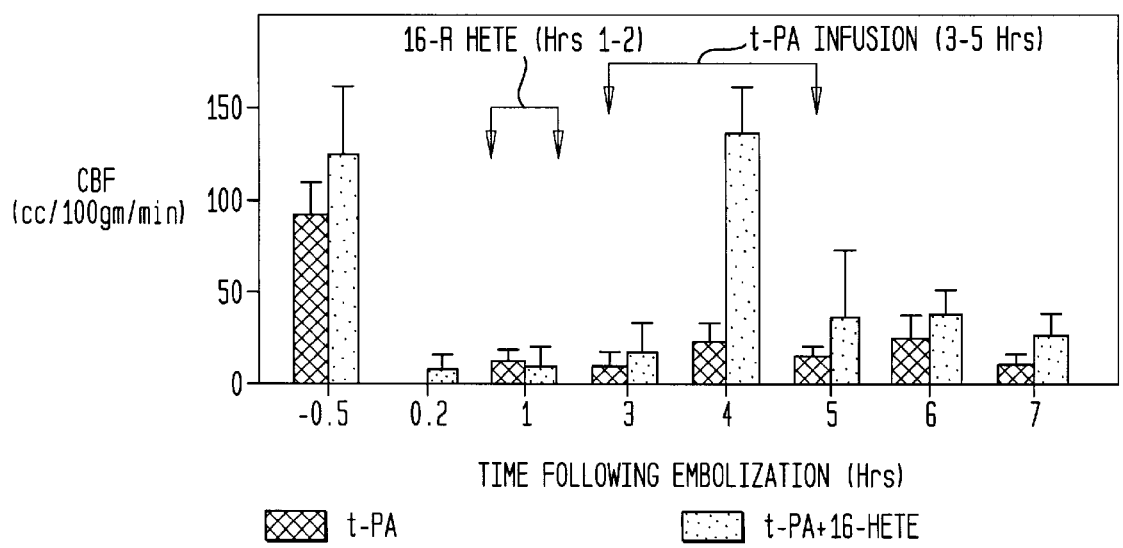
FIG. 4 is a bar graph depicting regional cerebral blood flow (rCBF) immediately prior to (−0.5 hours) and at various time points following clot embolization in a rabbit model of acute stroke, treated with either tPA alone (cross-hatched bar) or tPA in combination with 16-HETE (solid bar), where the 16-HETE is administered between one and two hours after clot embolization and the tPA is administered between three and five hours after clot embolization.
Figure 5:
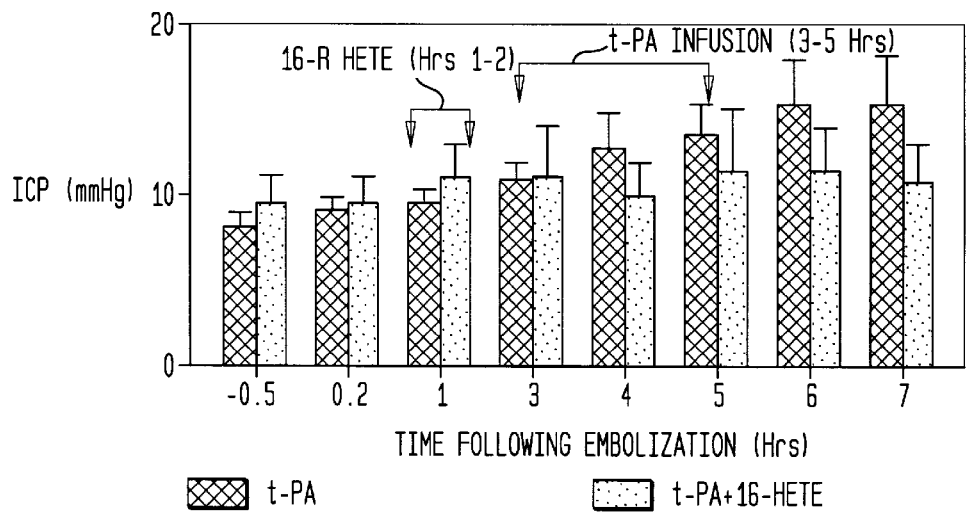
FIG. 5 is a bar graph depicting the intracranial pressure (ICP) immediately prior to (−0.5 hours) and at various time points following clot embolization in a rabbit model of acute stroke, treated with either tPA alone (cross-hatched bar) or tPA in combination with 16-HETE (solid bar), where the 16-HETE is administered between one and two hours after clot embolization and the tPA is administered between three and five hours after clot embolization.

Brain infarct size was measured following completion of the surgical procedure. Infarct size in both the tPA alone and vehicle groups was significantly larger than the 16-HETE and tPA group (FIG. 3). Brain infarct size was found to be related to the final regional cerebral blood flow (rCBF) value (FIG. 4). Animals in the 16-HETE and tPA group exhibited both the smallest infarct size and the greatest improvement in rCBF as a percentage of the base line value. 16-HETE also reduced intracranial pressure (ICP).(FIG. 5)

Example 5

16-HETE Transiently Decreases CD18 Receptor Density in Neutrophils

Methods

Animals were studied as described above in Example 4, except that the animals were administered 16-HETE alone at a dose of 1 mg/kg/min for one hour. Neutrophils were isolated at the following time points: 0.5 hour prior to embolization and 0.5, 1.5, 2.5 and 4 hours following embolization.

CD18 receptor density was determined by the following binding assay. Whole blood samples were collected at the time points outlined for the neutrophil activation studies. An aliquot of 100 µl from each sample was promptly treated with a saturating dose of primary monoclonal anti-CD 11/18 antibody (WMRD, Inc., Pullman, Wash.) at 1 µg/ $10^6$ cells. Following a thirty minute incubation at 4° C., each preparation was washed with 2 ml of cold Dulbecco's Phosphate Buffered Solution (Gibco BRL, Grand Island, N.Y.). It was then centrifuged for seven minutes at 7° C., 1500 rpm. After discarding the supernatants, a secondary monoclonal anti-IgG fluorescein conjugated antibody (Dako Corporation, Carpinteria, Calif.) was added to the samples. This was followed by a second 30 minute incubation at 4° C. The preparations were rewashed and centrifuged in the same manner as previously stated. Again discarding the supernatant, 250 µl of Optilyse C (Immunotech, Inc., Westbrook, Ma.) was added to lyse the erythrocytes and fix the remaining cells and antibody reactions. The cells next incubate at room-temperature for twenty minutes, and were rewashed and centrifuged for the final time. After removal of the supernatant, the cells were resuspended in 1 ml of 2% formalin (Baxter Healthcare Corporation, McGaw park, Ill.) diluted in DPBS. Throughout the study, three additional samples were prepared using a primary murine IgGI antibody (Caltag Laboratories, Burlingame, Calif.). Its use in place of the primary monoclonal anti-CD 11/18 antibody, served as an isotypic control ('IC') to estimate nonspecific binding of the primary antibody. The IC samples were processed in the same manner as those above. All final samples were wrapped in foil and stored at 4° C. in preparation for flow cytometric analysis the following morning. Total sample analysis on the Coulter Epics Elite requires thirty minutes. Neutrophils were identified by their distinctive forward versus side scattered signal. The CD 11/18 positivity was determined based upon these gated events. A standard curve was generated using Quantum 26 Fluorescent Beads (Flow Cytometry Standards Corporation, San Juan, PR). Actual MESF values were determined using the Quick-Cal 2.0 software package (Flow Cytometry Standards Corporation).

Results

Figure 6:
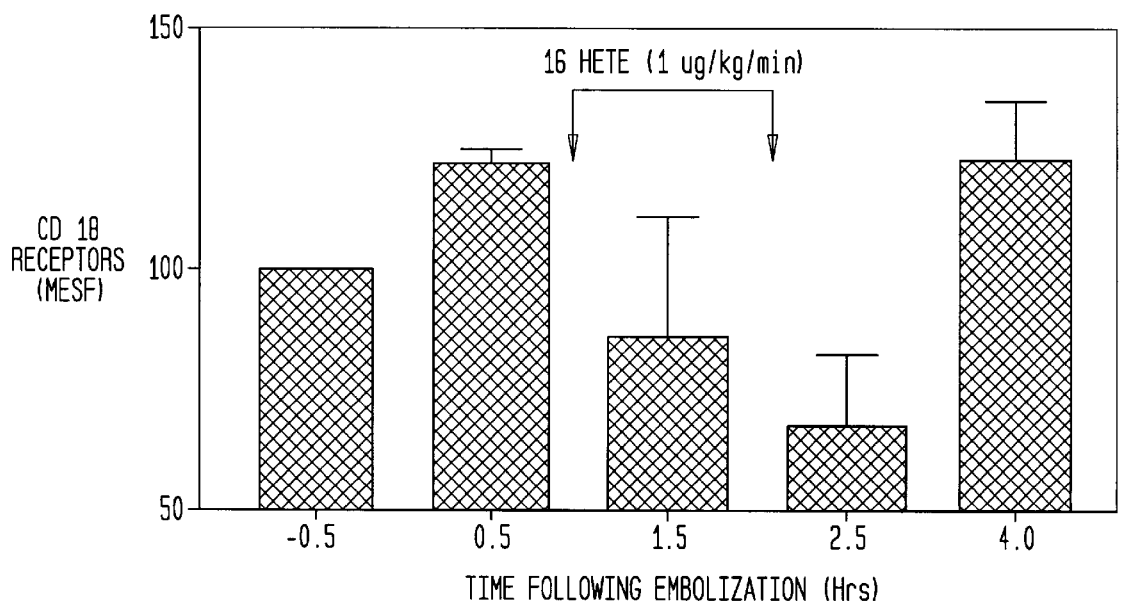
FIG. 6 is a bar graph depicting CD18 receptor density on the surface of neutrophils isolated at various time points following clot embolization from a rabbit model of acute stroke, treated with 16-HETE for one hour, beginning one hour after clot embolization.

The ability of a neutrophil to adhere to a vessel wall is mediated by CD1 8 receptors on the neutrophil surface. Following clot embolization in an animal model of acute stroke, CD18 receptor density is significantly increased, causing an increase in the ability of a neutrophil to adhere to a vessel wall. When 16-HETE is administered after clot embolization, CD18 receptor density was found to decrease significantly (FIG. 6). The decrease in CD18 receptor density occurred immediately after the administration of 16-HETE and was transient. After 16-HETE administration was stopped, CD18 receptor density returned to pretreatment levels.

The fact that the change in CD18 density in response to 16-HETE treatment is so rapid and is transient holds important clinical significance for the treatment of acute stroke. Neutrophils serve many important physiological functions in regulating inflammation. Although it is important to reduce neutrophil aggregation for the treatment of acute stroke, it is important to be able to restore neutrophil activity quickly if necessary. The regulation of neutrophil function is a delicate balance which could easily upset the physiological mechanisms involved in many processes. This balance is not easy to a achieve using drugs with prolonged activity. Therefore, the discovery that 16-HETE induces a rapid physiological response which is halted immediately after removal of the drug has important clinical significance.

Example 6

16-HETE Transiently Decreases CD18 Receptor Density in Neutrophils

Methods

Neutrophil $LTB_4$ Production

16(R)-HETE (0.01–1.0 μM) was preincubated for 10 minutes with the neutrophil suspension ($3 \times 10^6$ /ml) prior to the addition of formyl-methionyl-leucyl-phenylalanine (fMLP). Samples were then incubated for an additional 10 minutes with $5 \times 10^{-7}$M fMLP. All incubations took place at 37° C. Plasma samples for the measurement of $LTB_4$ were collected by centrifugation of the whole blood samples at 1200 rpm for 15 minutes. Samples were stored at 70° C. until analyzed. The plasma was then acidified to pH3 with 1M Hcl. The plasma was then placed on C2 reverse phase columns (Amprep for Amersham Corp., Arlington Heights, Ill.) to extract $LTB_4$. $LTB_4$ was then measured using the Biotrak $LTB_4$ enzyme immunoassay system (Amersham Corp., Arlington Heights, Ill.). All standards and samples were performed in duplicate. Following incubation, all samples were read at 450 nm and the $LTB_4$ concentration in each sample was determined following the generation of a standard curve. $LTB_4$ concentration was expressed as picograms $LTB_4$ per 1000 neutrophils.

Results

Figure 7:
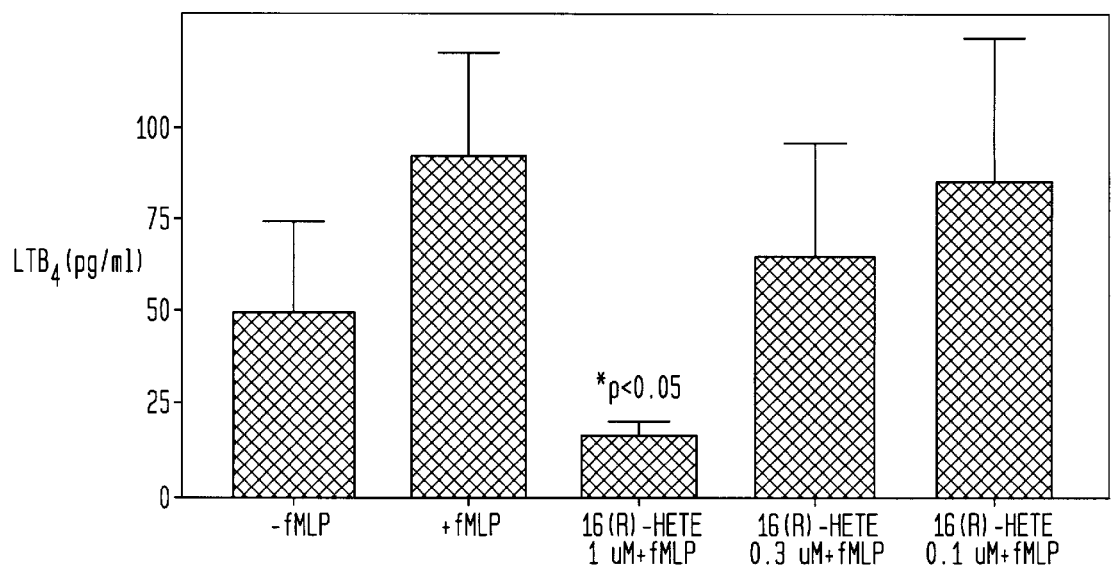
FIG. 7 is a bar graph depicting leukotriene $B_4$ synthesis in neutrophils treated with fMLP (formyl-methionyl-leucyl-phenylalanine) alone or in the presence of differing concentrations of 16-(R)HETE.

The addition of fMLP ($5 \times 10^{-7}$M) to isolated PMN suspensions resulted in an approximate doubling of the $LTB_4$ synthesis with levels of 92.8±27.1 pg/1000 neutrophils noted in the stimulated group when compared to a level of 49.9±24.2 pg/1000 PMNs in the unstimulated control group (FIG. 7). Preincubation with 16(R)-HETE resulted in a dose related inhibition of $LTB_4$ synthesis that was nearly complete at a concentration of 1 μM (17.0±3.2 pg/1000 neutrophils; p<0.05; n=4).

16-HETE potently suppressed $LTB_4$ production in neutrophils. $LTB_4$ is a potent neutrophil chemoattractant and pro-aggregant (Ford-Hutchinson, A. W.; Bray, M. A.; Doig, M. V.; Shipley, M. E.; and Smith, M. J. H. Leukotriene B, a potent chemokinetic and aggregating substance released from polymorphonuclear leukocytes. *Nature* 286:264–265 (1980). The inhibition of $LTB_4$ by 16-HETE contributes to its suppression of neutrophil activation. Thus the present studies support a regulatory role for 16-HETE in neutrophil function. It should be noted that the major cytochrome P450 product in neutrophils, 20-HETE, had no activity when examined in assays of neutrophil aggregation, adhesion or luminol chemiluminescence at concentrations up to 1 μM.

Example 7

Synthesis of 16-HETE Analogs

Methods

An equimolar mixture of 16-hydroxyeicosatetracnoic acid (16 HETE) and N-hydroxysuccinimide in anhydrous tetrahydrofuran (THF) was cooled to 0° C. To this was added 1 equivalent of dicyclohexylcarbodiimide (DCC) with stirring. After 12 h at room temperature, the solvent was removed in vacuo and the residue was purified by $SiO_2$ chromatography to afford the corresponding 16-HETE N-hydroxysuccimide ester in 75% yield as a colorless oil.

The above active ester (1 equivalent), methanesulfonamide (10 equivalents), and 4-(dimethylamino)pyridine (1 equivalent) were heated at 90 ° C. for 1.5 h in a minimum of dry hexamethylphosphoramide (HMPA). The cooled reaction mixture was added to water and extracted 3 times with EtOAc. The combined organic extracts were evaporated in vacuo and the residue purified by $SiO_2$ chromatography to afford N-methylsulfonyl-16-hydroxyeicosa-5,8,11,14-(Z)-tetraenamide as a colorless oil in 54% yield.

Example 8

Methods

To a compound (YKR-II-230-30) (2–55 mmol; 500 mg) in solvent THF: HMPA mixture (4:1 total 40 ml) at −40° C. $^7$BuLi (3.06 m mole; 2.5 solution in Hexane) was added dropwise and stirring was continued for 1 hr at same temperature. Then bromide (JY-I-27-20) (3.06 mmol; 1.572 gms) in THF (5 ml) was added at −40° C. and reaction mixture slowly allowed to room temperature and stirring was continued for overnight. Then reaction mixture cooled to 0° C., quenched with sat, aq, NhuCI solution, extracted with ether, washed with water, brine, dried over $Na_2SO_4$, concentrated and purified on silicagel column chromatography using EtoAc and N-Hexane or elements to get pure YKR-II-258-34 in 76% yield (1–22 gms) as colorless liquid.

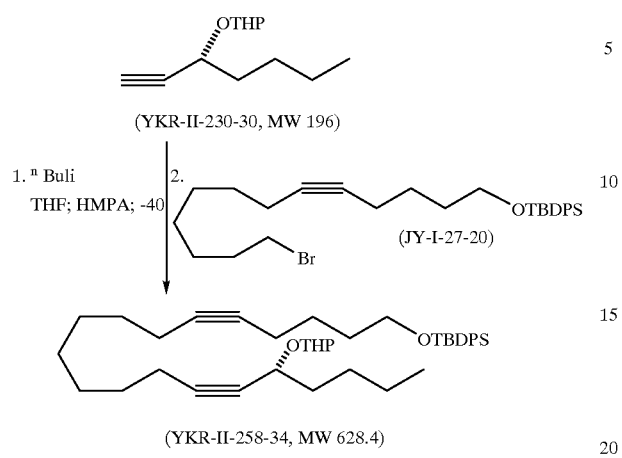

(YKR-II-230-30, MW 196)

(JY-I-27-20)

(YKR-II-258-34, MW 628.4)

Example 9

Methods

To a solution of compound (YKR-II-258-34) (0.64 mmole, 400 mg) in THF (15) ml at 0° C. TBAF (Tetrabutyl Ammonium Fluoride) (3.183 mmol; 1.0 m solution in THF; 3.183 ml) was added. Then reaction mixture was allowed to room temperature and stirrings was continued for overnight. Then solvent was removed under vacuum, diluted with $CH_2J_2$, washed with water, brine, dried over $Na_2SO_4$ and concentrated. The residue was purified on silicagel column chromatography using EtoAc and N-Hexane or elements to get pure YKR-II-258-34 in 87% yield (216 mg) as colorless syrup.

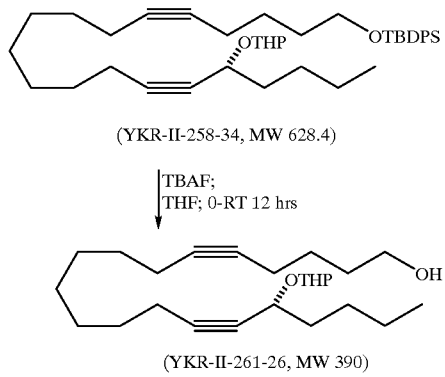

(YKR-II-258-34, MW 628.4)

TBAF;
THF; 0-RT 12 hrs (YKR-II-261-26, MW 390)

Example 10

Methods

To a solution of compound (YKR-II-261-26) (0.26 mmol; 100 mg) in DMF (5 ml) at room temperature PDC (Pydridinium diclomate)(1.28 mmole; 4.82 mg) was added and stirring was continued for 14 hours at same temperature. Reaction mixture then diluted with ether, washed with water, brine, dried over $Na_2SO_4$ and concentrated. Then the residue was treated with $CH_2N_2$ at 0° C. in $Et_2O$:MeOH (4:1) (total:10 ml) mixture. Then solvent was removed under vacuum and the residue was purified on silicagel column chromatography using EtoAc and N-Hexane solvents to get YKR-II-263-36 in 66% yield (70 mg).

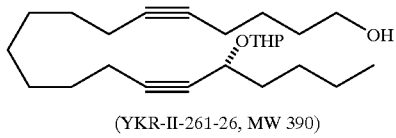

(YKR-II-261-26, MW 390)

1. PDC; DMF  2. $CH_2N_2$
RT; 14 hrs     MeOH: $Et_2O$ (1:4)
               0

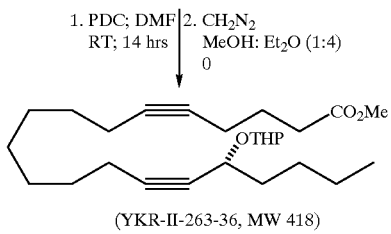

(YKR-II-263-36, MW 418)

Example 11

Methods

To a solution of compound (YKR-II-263-36) (0.099 mmol; 40 mg) in Methanol (20 ml) at 0° C. catalytic amount of PTSA (P-Towene Sulphonic acid) was added and reaction mixture allowed to room temperature. Stirring was continued for 2 hrs. Solvent was removed under vacuum, residue was dissolved in EtoAc, washed with $NaHCO_3$ solution, brine, dried over sat. aq. $Na_2SO_4$ and concentrated. The crude residue was purified on PTLC to get the pure compound YKR-II-266-31 in 92% yield (29 mg).

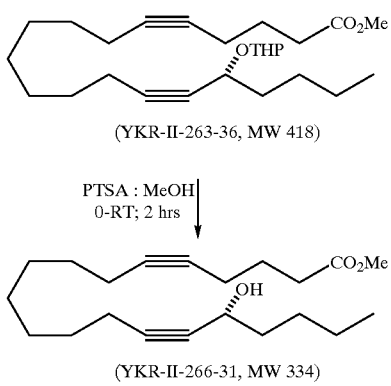

(YKR-II-263-36, MW 418)

PTSA : MeOH
0-RT; 2 hrs (YKR-II-266-31, MW 334)

Example 12

Methods

To a solution of compound YKR-II-266-31 (0.016 mmole: 5.2 mg) in THF:$H_2O$ mixture (5:1; Total 5 ml) at 0° C., 1.0 m solution of aq. LiOH (0.047 mmole; 47 ml) was added and reaction mixture allowed to room temperature. Stirring was continued for 12 hrs; the reaction mixture cooled to 0° C., neutralized with 1.0 m aq. oxalic acid solution. Volatiles were removed, diluted with EtoAL, washed with water, brine, dried over $Na_2$ $SO_4$, concentrated and purified on PTLC to get YKR-II-285-27 in 82% (4 mg) yield.

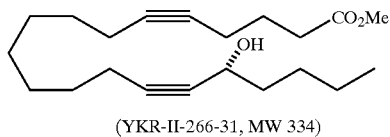

(YKR-II-266-31, MW 334)

1.0 M Aq. LiOH
THF:H₂O (5:1)
0-RT; 12 hrs

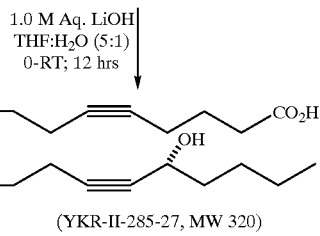

(YKR-II-285-27, MW 320)

Example 13

Methods

To a stirred solution of Nickelacetate tetrahydrate (0.04 mmoles; 9.9 mg) in EtOH(20 ml)at room temperature NaBHu (0.04 mmoles; 1.3 mg) was added under Hydrogen atmosphere. After 30 minutes stirring Ethylene diamine (0.08 mmoles: 5.3 ml) was added, followed by addition of compound (YKR-II-258-34)(0.79 mmoles; 500 mg). After two hours of stirring, reaction mixture diluted with others and filtered through bed of silicagel solvent was removed under reduced pressure. Crude mixture was purified on silicagel column chromatography using EtoAc and N-Hexane or element to get the pure compound YKR-II-262-27 in 93% yield as a colorless syrup.

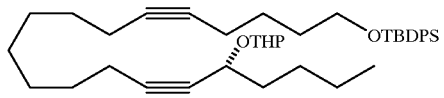

(YKR-II-258-34)

P2-Ni/H₂
EtOH; RT

(YKR-II-262-27, MW 632.4)

Example 14

Methods

To a solution of compound (YKR-II-262-27) (0.08 mmoles; 50 mg) in THF (10 ml) at 0° C. TBAF (Tetrabutyl ammonium fluoride) (0.40 mmoles; 1.0 m solution in THF: 400 ml) was added. Then reaction mixture allowed to room temperature and stirring was continued for overnight. The solvent was removed under vacuum, diluted with CH₂J₂, washed with water, brine, dried over Na2SO4, concentrated and the residue was purified on PTLC to get the pure compound YKR-II-280-26 in 85% yield (26.5 mg) as colorless syrup.

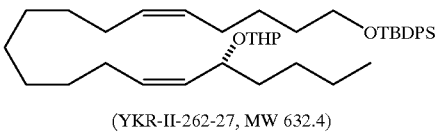

(YKR-II-262-27, MW 632.4)

TBAF in THF
0-RT; 12 hrs

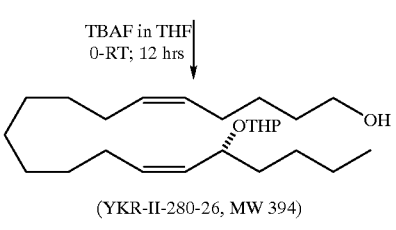

(YKR-II-280-26, MW 394)

Example 15

Methods

To a solution of compound (YKR-II-280-26) (0.05 mmoles; 20 mg) in methanol (5 ml) at 0° C., catalytic amount of PTSA (P-Towene Sulphonic Acid) was added and reaction mixture was allowed to room temperature. Stirring was continued for two hrs. Solvent was removed, residue was dissolved in EtoAc, washed with sat. aq. NaHCO₃ solution, brine, dried over Na₂SO₄ and concentrated. The crude residue was purified on PTLC to get YKR-II-251-25 in 92% yield (14.5 mg) as pure compound.

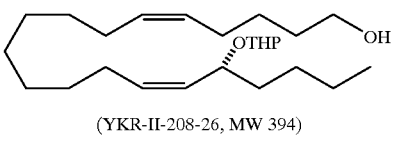

(YKR-II-208-26, MW 394)

PTSA; MeOH
0-RT, 2 hrs

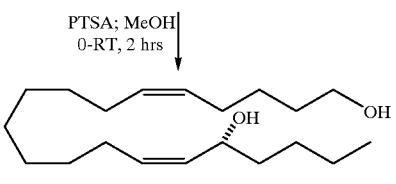

(YKR-II-281-25, MW 310)

Example 16

Methods

To a solution of compound (YKR-II-264-26) (0.13 mmoles; 50 mg) in DMF (5 ml) at room temperature PDC (Pyridinium dichromate)(0.63 mmoles; 238.7 mg) was added and stirring was continued for 16 hrs at same temperature. Then reaction mixture was diluted with ether, washed with water, brine, dried over Na₂SO₄ and concentrated. The residue was treated with CH₂N₂ at 0° C. in Et₂O MeOH (5:1) mixture. Solvent was removed and the residue was purified on PTLC to get YKR-II-282-34 as pure compound in 68% yield (36 mg).

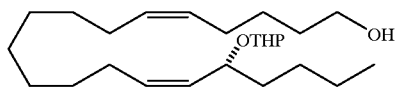

(YKR-II-264-26, MW 394)

1. PDC; DMF  2. CH$_2$N$_2$
RT; 16 hrs    Et$_2$O: MeOH (5:1)
              0

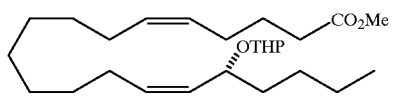

(YKR-II-282-34, MW 422)

Example 17

Methods

To a solution of compound (YKR-II-282-34) (0.05 mmoles; 20 mg) in methanol (10 ml) at 0° C. catalytic amount of PTSA was added and reaction mixture allowed to room temperature. Stirring was continued for 2 hrs. Solvent was removed, residue was dissolved in EtoAc, washed with sat. aq. NaHCO$_3$ solution, brine, dried over Na$_2$SO$_4$, concentrated and purified on PTLC to get the compound YKR-II-283-27 in 89% yield (14.3 mg).

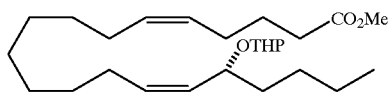

(YKR-II-282-34, MW 422)

PTSA:MeOH
0-RT; 2 hrs

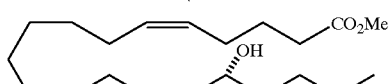

(YKR-II-283-27, MW 338)

Example 18

Methods

To a solution of compound (YKR-II-283-27) (0.013 mmoles; 4.4 mg) in THF: H20 mixture (5:1; Total 5 ml) at 0° C., 1.0 m solution fo aq. LiOH (0.039 mmoles, 39 ml) was added and reaction mixture allowed to room temperature. Stirring was continued for overnight. Then reaction mixture recooled to 0° C., neutralized with 1.0 m aq. oxalic acid solution. Volatiles were removed, diluted with EtoAc, washed with water, brine, dried over Na$_2$SO$_4$, concentrated and the residue was purified on PTLC to get the compound YKR-II-284-27 in 86% yield (3.6 mg).

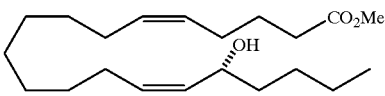

(YKR-II-283-27, MW 338)

1.0 M Aq. LiOH
THF:H$_2$O (5:1)
0-RT; 12 hrs

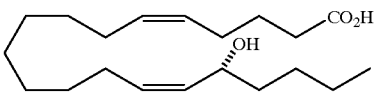

(YKR-II-284-27, MW 324)

Example 19

Methods

To a solution of compound (YKR-II-267-26) (0.07 mmoles; 30 mg) in methanol (5 ml), 10% pd-c (5 mg) was added and reaction mixture was stilTed under hydrogen atmosphere for 2 hrs. Then reaction mixture filtered through a pad of celite, concentrated and purified on PTLC to get the compound YKR-II-271-28 in 94% yield (28.7 mg) as white solid.

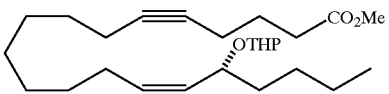

(YKR-II-267-26, MW 418)

Pd-c/H$_2$
MeOH; RT 2 hrs

(YKR-II-271-28, MW 426)

Example 20

Methods

To a solution of compound YKR-II-271-28 (0.047 mmoles, 20 mg) in methanol (5 ml) at 0° C., catalytic amount of PTSA was added. Reaction mixture then allowed to room temperatures, stirring was continued for 2 hrs. Solvent was removed, diluted with EtoAc, washed with sat. aq. NaHCO$_3$ solution, brine, dried over Na2SO$_4$, concentrated and the residue was purified on PTLC to get the compound (YKR-II-272-26) in 87% yield (14 mg) as white solid.

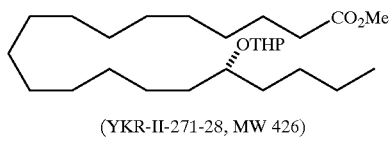

(YKR-II-271-28, MW 426)

PTSA; MeOH
0-RT; 2 hrs

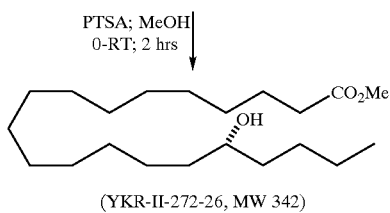

(YKR-II-272-26, MW 342)

Example 21

Methods

To a solution of compound YKR-II-272-26 (0.014 mmoles, 4.9 mg) in THF: $H_2O$ mixture (5: 1; Total 5 ml) at 0° C., 1.0 m solution of aq. LiOH (0.043 mmoles; 43 μl) was added and reaction mixture allowed to room temperature. Stirring was continued for 12 hrs. Then reaction mixture recooled to 0° C. and neutralized with 1.0 m. aq. oxalic acid with water, brine, dried over Na2SO4, concentrated and the residue was purified on PTLC to get the compound YKR-II-286-27 in 85% yield (4.0 mg) as white solid.

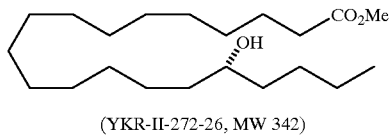

(YKR-II-272-26, MW 342)

1.0 M Aq. LiOH
THF:$H_2O$ (5:1)
0-RT; 12 hrs

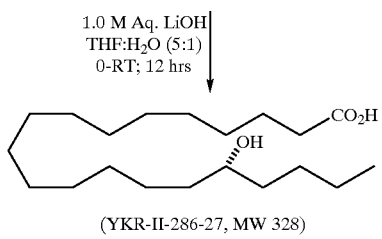

(YKR-II-286-27, MW 328)

Example 22

16-HETE Analogs Which Retain Neutrophil Inhibiting Activity of 16-HETE

Methods

The methods were performed as described above in Example 3.

Results

Figure 8:
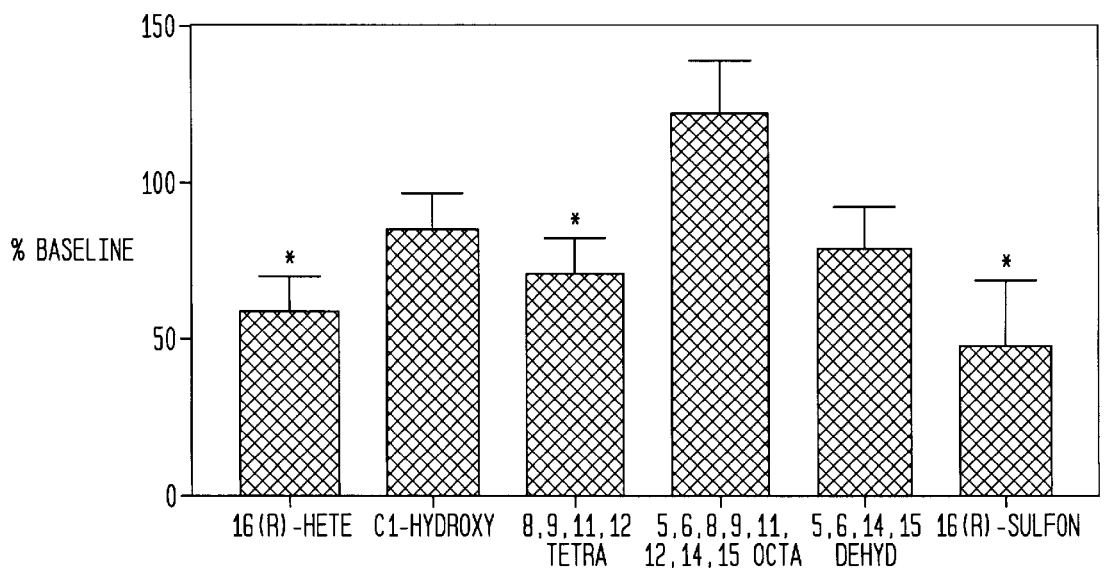
FIG. 8 is a bar graph depicting the ability of 16-HETE agonists to inhibit fMLP-induced neutrophil aggregation.

In order to demonstrate the biological effects of 16-HETE on human neutrophils, neutrophil aggregation was analyzed after preincubation of 16-HETE(R) and 5 separate 16-HETE analogs. At concentrations of one micromolar, 16-HETE (R) and each analog inhibited FMLP-induced neutrophil aggregation (Table 3 and FIG. 8). The data is based on four independent observations per compound tested. Although the sulfonamide derivative had slightly lower activity than 16-HETE (R), it still demonstrated significant therapeutic potential.

TABLE 3

The effect of preincubation with 16(R)-HETE and 16-HETE analogs on neutrophil aggregation

|   | Aggregation |
| --- | --- |
| 16(R)-HETE | 42.0 ± 11.0* |
| 8,9,11,12-tetrahydro-16(R)-HETE | 71.1 +/− 10.3* |
| 5,6,14,15-Dehydro-8,9,11,12-tetrahydro-16(R)-HETE | 79.4 +/− 12.2 |
| C(1)-hydroxyl 16-HETE | 84.6 +/− 11.4 |
| 5,6,8,9,11,12,14,15-octahydro-16(R)-HETE | 122.8 +/− 15.4 |
| 16(R)-HETE sulfonimide | 47.6 +/− 20.5* |

Values represent percent of inhibition from HETE untreated cells (N = 4 in each group). 1 mM concentrations of compound was used for each analysis.
*($p < 0.05$)

The biological effects of 16-HETE on human neutrophils have not been previously reported. 16(R)-HETE displayed a potent inhibitory activity towards unstimulated and stimulated neutrophils. The biological effect observed with 16(R)-HETE was more potent than the effect observed with the other stereoisomer, 16(S)-HETE. 16(R)-HETE inhibited neutrophil adhesion, basal and thrombin-stimulated, and fMLP-induced neutrophil aggregation.

Example 23

16-HETE does not Affect Platelet Function

Methods

Platelet aggregation was examined in diluted whole blood using a Chronology whole blood aggregometer (Havertown, Pa.) as previously described (Bednar, M. M.; Dooley, R. H.; Zamani, M.; Howard, D. B.; and Gross, C. E. Neutrophil and platelet activity and quantification following delayed t-PA therapy in a rabbit model of thromboembolic stroke. *J. Thromb. Thrombol.* 1:179–185 (1995). Briefly, whole blood was collected in 3.8% sodium citrate (9:1, v/v) and was subsequently diluted 50:50 with normal saline. Aggregation was assessed over a 6 minute interval following addition of a submaximal concentration of adenosine diphosphate (ADP, 5 μM: Sigma Corporation, St. Louis, Mo.). Aggregation was then repeated following a ten minute incubation with either 1 μM or 16(R)-HETE or 16(S)-HETE and expressed as the change in impedance as a percentage of the baseline value. Adenosine triphosphate (ATP) release was simultaneously measured from ADP-stimulated platelets in the Chronology whole blood aggregometer using the Chrono-Lume luminescent agent (firefly luciferin-luciferase). Samples were compared to chemiluminescence obtained from ATP standards following the addition of luciferin-luciferase.

Results

No significant effect of either 16(R)-HETE or 16(S)-HETE was seen on platelet function at a concentration of 1 μM (n=3, mean±sem). When compared to ATP release in control samples, 16(R)-HETE and 16(S)-HETE released 99.3±0.7 and 108.0±6.8% of the control sample respectively. Similarly, ADP-induced platelet aggregation following incubation with 1 μM 16(R)- and 16(S)-HETE was 85.9±21.4 and 101.3±14.0% of the control value, respectively.

Various metabolites of arachidonic acid demonstrates overlapping profiles of biological activity. It has previously been demonstrated at 15-HETE (Takata, S.; Matsubara, M.; Allen, P. G.; Janmey, P. A.; Serhan, C. N.; Brady, H. R. Remodeling of neutrophil phospholipids with 15(S)-hydroxyeicosatetracnoic acid inhibits leukotriene B4-induced neutrophil migration across endothelium. *J.*

Clin. Invest. 93:499–508 (1994); Petrich, K.; Ludwig, P.; Kuhn,; H.; Schewe, T. The suppression of 5-lipoxygenation of arachidonic acid in human polymorphonuclear leukocytes by the 15-lipoxygenase product 15(S)-hydroxy-5Z, 8Z, 11Z, 13E)-cicosatetraenoic acid: structure-activity relationship and mechanism of action. *Biochemical Journal* 314:911–6 (1996); and Huang, Z. H.; Bates, E. J.; Ferrante, J. V.; Hii, C. S. T.; Poulos, A.; Robinson, B. S.; and Ferrante, A. Inhibition of stimulus-induced endothelial cell intercellular adhesion molecule-1, E-selectin, and vascular cellular adhesion molecule-1 expression by arachidonic acid and its hydroxy and hydroperoxy derivatives. *Cir. Res.* 80:149–158 (1997) and prostacyclin (Darius, H.; Veit, K.; Binz, C.; Fish, A.; and Meyer, J. Diminished inhibition of adhesion molecule expression in prostacyclin receptor desensitized human platelets. *Agents & Actions* 45:77–83 (1995); and Boxer, L. A.; Allen, J. M.; Schmidt, M.; Yoder, M.; and Baehner, R. L. Inhibition of polymorphonuclear leukocyte adherence by prostacyclin. *J. Laboratory & Clinical Med.* 95:672–678 (1980) may both downregulate adhesion receptors and suppress neutrophil function. Although suppression of neutrophil function is shared by various eicosanoids, including 16-HETE in the present study, the 16-HETE biological activity appears to be relatively specific for the neutrophil as prostacyclin inhibits platelet activation (Tateson, J. E.; Moncada, S.; Vane, J. R. Effects of prostacyclin (PGX) on cyclic AMP concentrations in human platelets. *Prostaglandins* 13:389–397 (1977)) whereas 15-HETE has been demonstrated to increase platelet activation (Setty, B. N.; Werner, M. H.; Hannun, Y. A.; and Stuart, M. J. 15-Hydroxyeicosatetracnoic acid-mediated potentiation of thrombin-induced platelet functions occurs via enhanced production of phosphoinositide-derived second messengers—-sn-1,2-diacylglycerol and inositol-1,4,5-triphosphate. *Blood* 80:2765–2773 (1992)). Studies in our laboratory also suggest that 16-HETE does not possess significant vasoactive properties unlike the significant hypotension seen with prostacyclin (Armstrong, J. M.; Lattimer, N.; Moncada, S.; and Vane, J. R. Comparison of vasodepressor effects of prostacyclin and 6-oxo-prostaglandin F1 alpha with those of prostaglandin E2 in rats and rabbits. *Brit. J. Pharm.* 62:125–130 (1978)) in vivo or enhanced the vascular reactivity seen with 15-HETE in vitro (Uski, T. K.; and Hogestatt, E. D. Effects of various cyclooxygenase and lipoxygenase metabolites on guinea-pig cerebral arteries. *Gen. Pharm.* 23:109–113 (1992) and Van Diest, M. J.; Herman, A. G.; and Verbeuren, T. J. Influence of hypercholesterolemia on the reactivity of isolated rabbit arteries to 15-lipoxygenase metabolites of arachidonic acid: comparison and platelet-derived agents and vasodilators. Prostaglandins Leukocytes & Essential Fatty Acids 54: 135–145 (1996)). This relative specificity for neutrophil function is advantageous in both determining cell mechanisms as well as designing therapies for various ischemic states.

STATISTICS

Student's t test was used to compare control versus 16-HETE-treated samples. Differences were considered significant at the $p<0.05$ level.

Each of the foregoing patents, patent applications and references that are recited in this application are herein incorporated in their entirety by reference. Having described the presently preferred embodiments, and in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

We claim:

1. A compound of a 16-hydroxyeicosatetraenoic acid analog comprising a compound selected from the group consisting of:

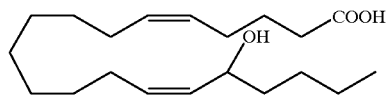

2. The compound of claim 1 wherein the 16-hydroxyeicosatetraenoic acid analog is an agonist having the following structure:

3. The compound of claim 1 wherein the 16-hydroxyeicosatetraenoic acid analog is an agonist having the following structure:

* * * * *

UNITED STATES PATENT AND TRADEMARK OFFICE
CERTIFICATE OF CORRECTION

PATENT NO. : 6,359,158 B1
DATED : March 19, 2002
INVENTOR(S) : Falck et al.

It is certified that error appears in the above-identified patent and that said Letters Patent is hereby corrected as shown below:

Column 1,
Line 6, between the first paragraph and the "FIELD OF THE INVENTION" paragraph, insert

-- GOVERNMENT SUPPORT

The invention was developed at least in part using Federal Funding under a grant from the National Institutes of Health under Grant Number NS31008 and NS28708. Accordingly, the government may have rights in the invention. --

Column 8,
Line 64, delete the word "fMLP-included" and replace with the word
-- fMLP-induced --.

Column 14,
Line 2, delete the word "metacyclinc" and replace with the word -- metacycline --.
Line 25, delete the word "cefinenoxime" and replace with the word
-- cefmenoxime --.

Column 15,
Line 29, delete the word "antitlirombin" and replace with the word -- antithrombin --.
Line 37, delete the word "Hennevekens" and replace with the word -- Hennekens --.

Column 16,
Line 47, delete the word "scrine" and replace with the word -- serine --.

Column 21,
Line 46, delete the word "cluted" and replace with the word -- eluted --.

Column 22,
Line 36, delete the word "clromatographic" and replace with the word
-- chromatographic --.

Column 23,
Line 10, delete the word "Eglinlon" and replace with the word -- Eglinton --.

UNITED STATES PATENT AND TRADEMARK OFFICE
CERTIFICATE OF CORRECTION

PATENT NO. : 6,359,158 B1
DATED : March 19, 2002
INVENTOR(S) : Falck et al.

It is certified that error appears in the above-identified patent and that said Letters Patent is hereby corrected as shown below:

Column 24,
Lines 19-20, delete the word "neutrolphilphospholipids" and replace with the word -- neutrophilphospholipids --.
Line 58, delete the word "aldchyde" and replace with the word -- aldehyde --.

Column 25,
Line 55, delete the word "maimer" and replace with the word -- manner --.

Column 28,
Line 67, delete the word "Ma.)" and replace with the word -- ME.) --.

Column 29,
Line 7, delete the word "IgGI" and replace with the word -- IgG1 --.

Column 30,
Line 37, delete the word "hydroxyeicosatetracnoic" and replace with the word -- hydroxyeicosatetraenoic --.
Line 65, delete the word "NhuCI" and replace with the word -- NhuCl --.

Column 36,
Line 29, delete the word "stilTed" and replace with the word -- stirred --.

Column 37,
Line 62, delete the word "FMLP" and replace with the word -- fMLP --.

Column 38,
Line 46, delete the word "Chronology" and replace with the word -- Chronolog --.
Line 66, delete the word "hydroxyeicosatetrancnoic" and replace with the word -- hydroxyeicosatetraenoic --.

Column 39,
Line 5, delete the word "13E)-cicosatetraneoic" and replace with the word -- 13E)-eicosatetraneoic --.

UNITED STATES PATENT AND TRADEMARK OFFICE
CERTIFICATE OF CORRECTION

PATENT NO.    : 6,359,158 B1
DATED         : March 19, 2002
INVENTOR(S)   : Falck et al.

It is certified that error appears in the above-identified patent and that said Letters Patent is hereby corrected as shown below:

Column 40, after the structure existing as part of claim 1, add:

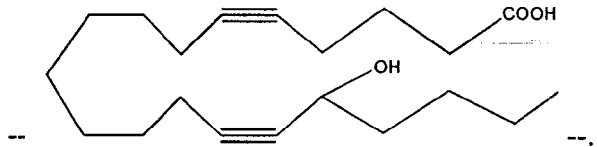

Signed and Sealed this

Third Day of June, 2003

JAMES E. ROGAN
*Director of the United States Patent and Trademark Office*